(12) United States Patent
Ariga et al.

(10) Patent No.: US 8,168,430 B2
(45) Date of Patent: May 1, 2012

(54) METHOD FOR PREPARATION OF HEPATOCYTE USING ES CELL

(75) Inventors: Toyohiko Ariga, Tokyo (JP); Taiichiro Seki, Tokyo (JP); Go Watanabe, Tokyo (JP); Hiroto Nakashima, Tokyo (JP); Yuichi Hasebe, Tokyo (JP)

(73) Assignee: Nihon University, Tokyo (JP)

( * ) Notice: Subject to any disclaimer, the term of this patent is extended or adjusted under 35 U.S.C. 154(b) by 496 days.

(21) Appl. No.: 12/225,411

(22) PCT Filed: Mar. 24, 2006

(86) PCT No.: PCT/JP2006/306783
§ 371 (c)(1),
(2), (4) Date: Sep. 22, 2008

(87) PCT Pub. No.: WO2007/110966
PCT Pub. Date: Oct. 4, 2007

(65) Prior Publication Data
US 2010/0055762 A1    Mar. 4, 2010

(51) Int. Cl.
*C12N 5/00* (2006.01)
*A01N 63/00* (2006.01)
(52) U.S. Cl. ........................................ 435/377; 435/402
(58) Field of Classification Search .................... None
See application file for complete search history.

(56) References Cited

U.S. PATENT DOCUMENTS

| 6,638,502 | B1 | 10/2003 | Li et al. | |
|---|---|---|---|---|
| 6,833,357 | B2 * | 12/2004 | Cines et al. | ...................... 514/12 |
| 2004/0191902 | A1 * | 9/2004 | Hambor et al. | ................ 435/370 |
| 2005/0170502 | A1 * | 8/2005 | Zern et al. | ....................... 435/370 |
| 2009/0010900 | A1 * | 1/2009 | Fair et al. | .................... 424/93.21 |

FOREIGN PATENT DOCUMENTS
WO    WO-98/49321 A2    11/1998

OTHER PUBLICATIONS

Tsuyoshi Watanabe, Japanese journal of Thrombosis and Hemostasis (2005), vol. 16, No. 5, p. 534.

* cited by examiner

*Primary Examiner* — Quang Nguyen
(74) *Attorney, Agent, or Firm* — Birch, Stewart, Kolasch & Birch, LLP

(57) ABSTRACT

This invention relates to an agent for promoting differentiation of an ES cell, preferably an agent for promoting differentiation of an ES cell into a hepatocyte or a prophylactic agent for teratoma, comprising uPA. Furthermore this invention relates to a method of promoting differentiation of an ES cell, preferably a method of promoting differentiation of an ES cell into a hepatocyte, comprising the step of contacting uPA with the ES cell, or a method of preparing a hepatocyte comprising the step of contacting uPA with an ES cell to differentiate the ES cell into a hepatocyte.

2 Claims, 14 Drawing Sheets
(10 of 14 Drawing Sheet(s) Filed in Color)

Fig. 3
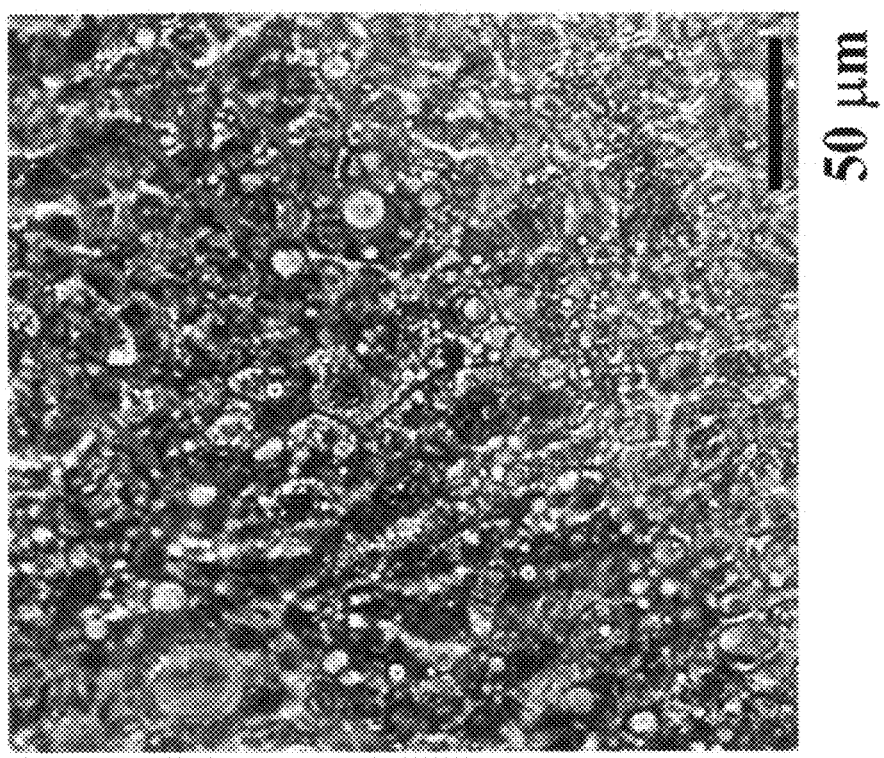
50 μm
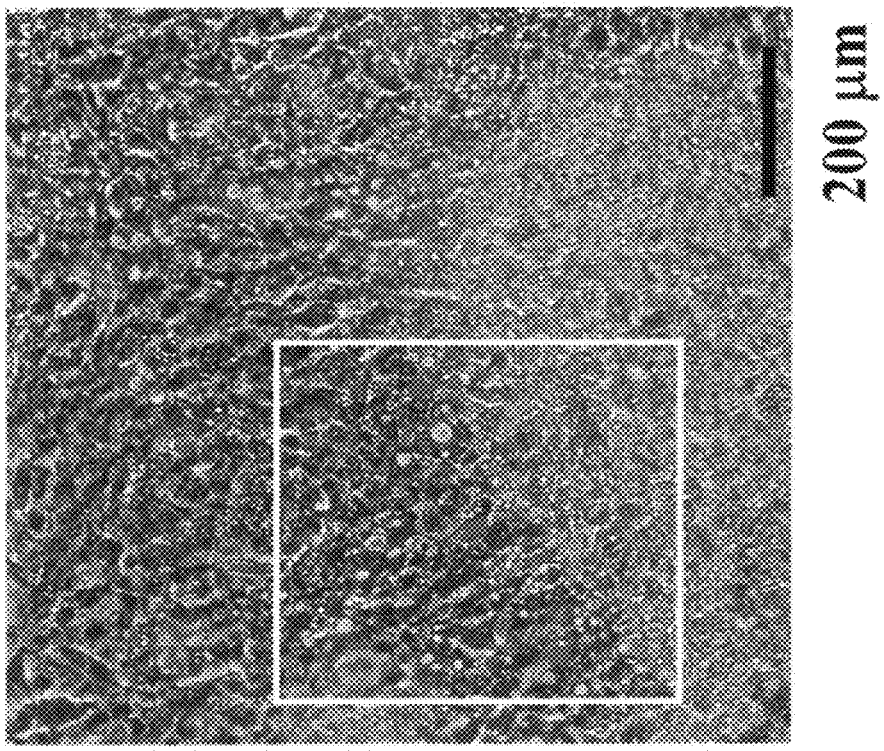
200 μm

Fig. 7
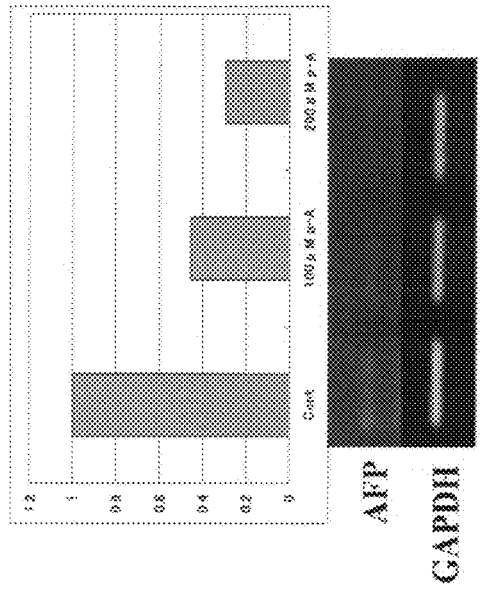
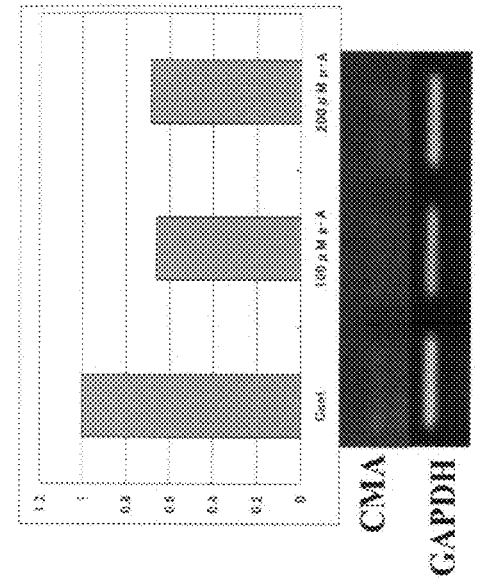
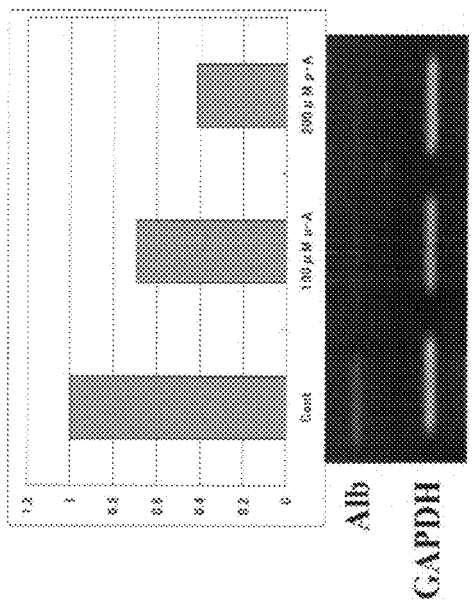
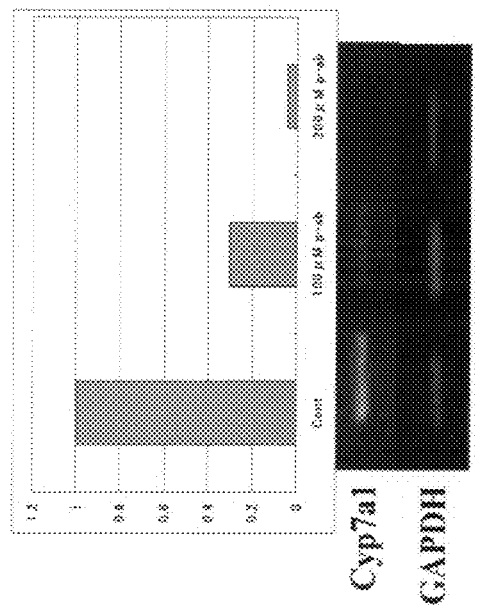

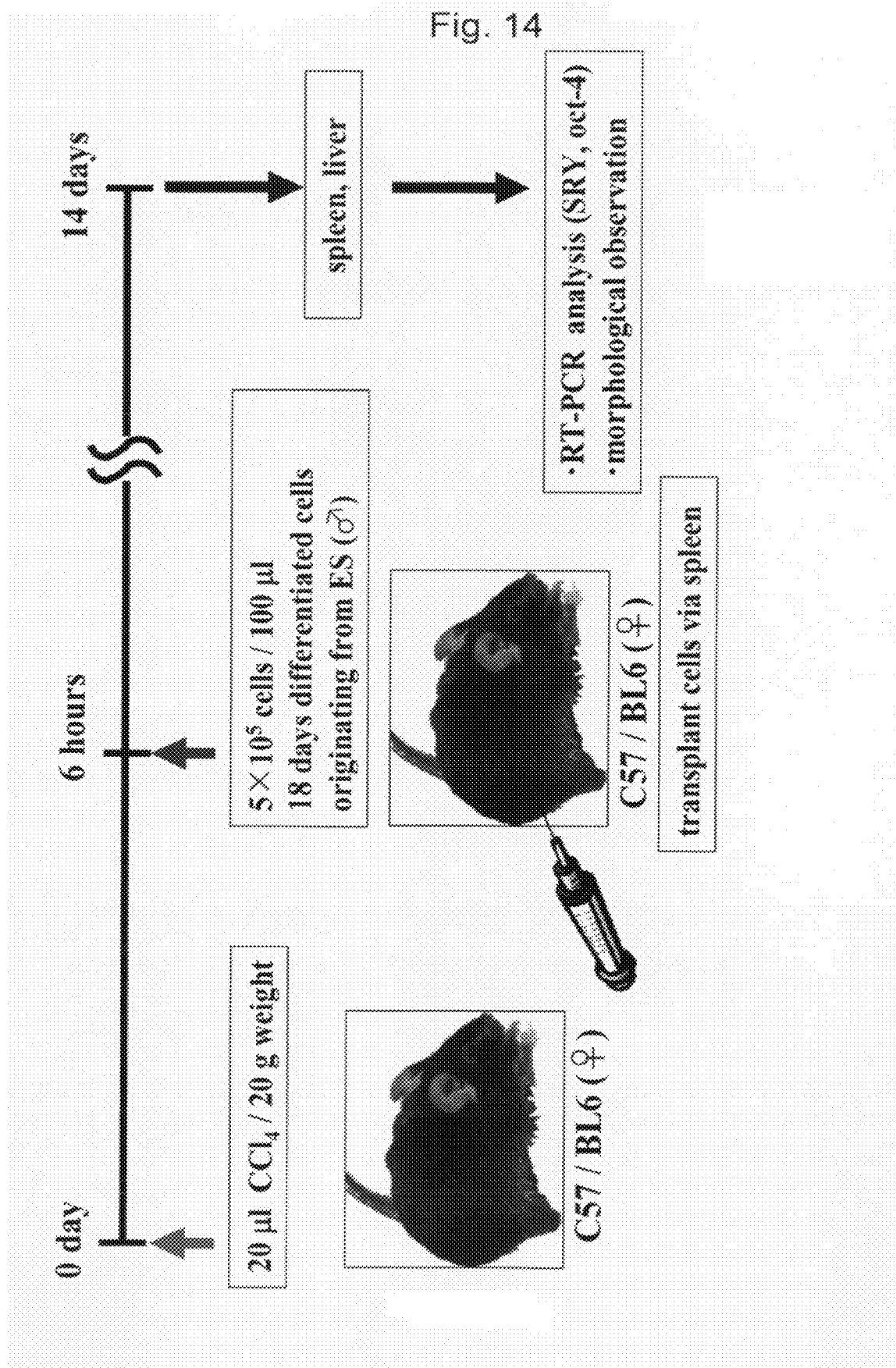

SEQUENCE LISTING

```
<160> NUMBER OF SEQ ID NOS: 24

<210> SEQ ID NO 1
<211> LENGTH: 1293
<212> TYPE: DNA
<213> ORGANISM: Homo sapiens

<400> SEQUENCE: 1
atgagagccc tgctggcgcg cctgcttctc tgcgtcctgg tcgtgagcga ctccaaaggc      60
agcaatgaac ttcatcaagt tccatcgaac tgtgactgtc taaatggagg aacatgtgtg     120
tccaacaagt acttctccaa cattcactgg tgcaactgcc caaagaaatt cggagggcag     180
cactgtgaaa tagataagtc aaaaacctgc tatgagggga atggtcactt ttaccgagga     240
aaggccagca ctgacaccat gggccggccc tgcctgccct ggaactctgc cactgtcctt     300
```

```
cagcaaacgt accatgccca cagatctgat gctcttcagc tgggcctggg gaaacataat    360
tactgcagga acccagacaa ccggaggcga ccctggtgct atgtgcaggt gggcctaaag    420
ccgcttgtcc aagagtgcat ggtgcatgac tgcgcagatg gaaaaaagcc ctcctctcct    480
ccagaagaat taaaatttca gtgtggccaa aagactctga ggccccgctt taagattatt    540 ggggagaat tcaccaccat cgagaaccag ccctggtttg cggccatcta caggaggcac    600
cgggggggct ctgtcaccta cgtgtgtgga ggcagcctca tcagcccttg ctgggtgatc    660
agcgccacac actgcttcat tgattaccca aagaaggagg actacatcgt ctacctgggt    720
cgctcaaggc ttaactccaa cacgcaaggg gagatgaagt ttgaggtgga aaacctcatc    780
ctacacaagg actacagcgc tgacacgctt gctcaccaca acgacattgc cttgctgaag    840
atccgttcca aggagggcag gtgtgcgcag ccatcccgga ctatacagac catctgcctg    900
ccctcgatgt ataacgatcc ccagtttggc acaagctgtg agatcactgg ctttggaaaa    960
gagaattcta ccgactatct ctatccggag cagctgaaaa tgactgttgt gaagctgatt   1020
tcccaccggg agtgtcagca gccccactac tacggctctg aagtcaccac caaaatgcta   1080
tgtgctgctg accccaatg gaaaacagat tcctgccagg gagactcagg ggacccctc    1140 gtctgttccc tccaaggccg catgactttg actggaattg tgagctgggg ccgtggatgt   1200
gccctgaagg acaagccagg cgtctacacg agagtctcac acttcttacc ctggatccgc   1260
agtcacacca aggaagagaa tggcctggcc ctc                                1293

<210> SEQ ID NO 2
<211> LENGTH: 431
<212> TYPE: PRT
<213> ORGANISM: Homo sapiens

<400> SEQUENCE: 2

Met Arg Ala Leu Leu Ala Arg Leu Leu Leu Cys Val Leu Val Val Ser
1               5                   10                  15

Asp Ser Lys Gly Ser Asn Glu Leu His Gln Val Pro Ser Asn Cys Asp
            20                  25                  30

Cys Leu Asn Gly Gly Thr Cys Val Ser Asn Lys Tyr Phe Ser Asn Ile
        35                  40                  45

His Trp Cys Asn Cys Pro Lys Lys Phe Gly Gly Gln His Cys Glu Ile
    50                  55                  60

Asp Lys Ser Lys Thr Cys Tyr Glu Gly Asn Gly His Phe Tyr Arg Gly
65                  70                  75                  80

Lys Ala Ser Thr Asp Thr Met Gly Arg Pro Cys Leu Pro Trp Asn Ser
                85                  90                  95

Ala Thr Val Leu Gln Gln Thr Tyr His Ala His Arg Ser Asp Ala Leu
            100                 105                 110

Gln Leu Gly Leu Gly Lys His Asn Tyr Cys Arg Asn Pro Asp Asn Arg
        115                 120                 125

Arg Arg Pro Trp Cys Tyr Val Gln Val Gly Leu Lys Pro Leu Val Gln
    130                 135                 140

Glu Cys Met Val His Asp Cys Ala Asp Gly Lys Lys Pro Ser Ser Pro
145                 150                 155                 160

Pro Glu Glu Leu Lys Phe Gln Cys Gly Gln Lys Thr Leu Arg Pro Arg
                165                 170                 175

Phe Lys Ile Ile Gly Gly Glu Phe Thr Thr Ile Glu Asn Gln Pro Trp
            180                 185                 190

Phe Ala Ala Ile Tyr Arg Arg His Arg Gly Gly Ser Val Thr Tyr Val
```

```
                195                 200                 205

Cys Gly Gly Ser Leu Ile Ser Pro Cys Trp Val Ile Ser Ala Thr His
    210                 215                 220

Cys Phe Ile Asp Tyr Pro Lys Lys Glu Asp Tyr Ile Val Tyr Leu Gly
225                 230                 235                 240

Arg Ser Arg Leu Asn Ser Asn Thr Gln Gly Glu Met Lys Phe Glu Val
                245                 250                 255

Glu Asn Leu Ile Leu His Lys Asp Tyr Ser Ala Asp Thr Leu Ala His
            260                 265                 270

His Asn Asp Ile Ala Leu Leu Lys Ile Arg Ser Lys Glu Gly Arg Cys
        275                 280                 285

Ala Gln Pro Ser Arg Thr Ile Gln Thr Ile Cys Leu Pro Ser Met Tyr
    290                 295                 300

Asn Asp Pro Gln Phe Gly Thr Ser Cys Glu Ile Thr Gly Phe Gly Lys
305                 310                 315                 320

Glu Asn Ser Thr Asp Tyr Leu Tyr Pro Glu Gln Leu Lys Met Thr Val
                325                 330                 335

Val Lys Leu Ile Ser His Arg Glu Cys Gln Gln Pro His Tyr Tyr Gly
            340                 345                 350

Ser Glu Val Thr Thr Lys Met Leu Cys Ala Ala Asp Pro Gln Trp Lys
        355                 360                 365

Thr Asp Ser Cys Gln Gly Asp Ser Gly Gly Pro Leu Val Cys Ser Leu
    370                 375                 380

Gln Gly Arg Met Thr Leu Thr Gly Ile Val Ser Trp Gly Arg Gly Cys
385                 390                 395                 400

Ala Leu Lys Asp Lys Pro Gly Val Tyr Thr Arg Val Ser His Phe Leu
                405                 410                 415

Pro Trp Ile Arg Ser His Thr Lys Glu Glu Asn Gly Leu Ala Leu
            420                 425                 430

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
cgtggctgta aaagtgttca                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
agagtcgttg gctgtgaaaa                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
cccccattct ctgaggataa                                              20
```

```
<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
ctttggaccc tcttctgtga                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
tgtccctctc tggaaactat                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
tgttgaagtt caggataggg                                              20

<210> SEQ ID NO 9
<211> LENGTH: 30
<212> TYPE: DNA
<213> ORGANISM: Artificial Sequence
<220> FEATURE:
<223> OTHER INFORMATION: Synthetic primer

<400> SEQUENCE: 9
ttcctccttt gcctcgctgg actggtattt                                   30

<210> SEQ ID NO 10
<211> LENGTH: 30
<212> TYPE: DNA
<213> ORGANISM: Artificial Sequence
<220> FEATURE:
<223> OTHER INFORMATION: Synthetic primer

<400> SEQUENCE: 10
gcgaattcat ggaacgggga aatgccaagt                                   30

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
accacagtcc atgccatcac                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer
```

<400> SEQUENCE: 12
tccaccaccc tgttgctgta                                       20

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
ggcgttctct ttggaaaggt gttc                                  24

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
ctcgaaccac atccttctct                                       20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
aagcagctca tggacatcaa                                       20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
cttttatcac cccagtcagg                                       20

<210> SEQ ID NO 17
<211> LENGTH: 18
<212> TYPE: DNA
<213> ORGANISM: Artificial Sequence
<220> FEATURE:
<223> OTHER INFORMATION: Synthetic primer

<400> SEQUENCE: 17
aggacttcac tctacacc                                         18

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
gcagtcgtta catcatcc                                         18

<210> SEQ ID NO 19
<211> LENGTH: 27
<212> TYPE: DNA

```
<213> ORGANISM: Artificial Sequence
<220> FEATURE:
<223> OTHER INFORMATION: Synthetic primer

<400> SEQUENCE: 19
cagttccacg accagcagct tacctac                                          27

<210> SEQ ID NO 20
<211> LENGTH: 29
<212> TYPE: DNA
<213> ORGANISM: Artificial Sequence
<220> FEATURE:
<223> OTHER INFORMATION: Synthetic primer

<400> SEQUENCE: 20
agccaggcat ctagtaagag tccttgacc                                        29

<210> SEQ ID NO 21
<211> LENGTH: 19
<212> TYPE: DNA
<213> ORGANISM: Artificial Sequence
<220> FEATURE:
<223> OTHER INFORMATION: Synthetic primer

<400> SEQUENCE: 21
aaatcactgc actggctcc                                                   19

<210> SEQ ID NO 22
<211> LENGTH: 19
<212> TYPE: DNA
<213> ORGANISM: Artificial Sequence
<220> FEATURE:
<223> OTHER INFORMATION: Synthetic primer

<400> SEQUENCE: 22
tgggcctgcc tcatcatac                                                   19

<210> SEQ ID NO 23
<211> LENGTH: 21
<212> TYPE: DNA
<213> ORGANISM: Artificial Sequence
<220> FEATURE:
<223> OTHER INFORMATION: Synthetic primer

<400> SEQUENCE: 23
ttcaatccca cattggagaa g                                                21

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
tcttttcagc ttcttccctc                                                  20
```

METHOD FOR PREPARATION OF HEPATOCYTE USING ES CELL

TECHNICAL FIELD

This invention relates to a method of promoting the differentiation of an ES cell and a method of preparing a hepatocyte using an ES cell.

BACKGROUND ART

The liver is the largest organ in the body and plays central roles in metabolisms in the body. The liver is the only organ in the body to be able to regenerate. It is known that even if 80% of the total liver weight is excised, the liver restore its capacity to the original weight.

At present, it is thought that the most effective method of treating serious chronic liver disorders, such as hepatitis C or liver cirrhosis which hinders functional liver regeneration, is a method of liver transplantation, in which a liver is transplanted from a liver provider (hereafter "donor"). Even hybrid-type of artificial livers or cell transplantation therapies requires liver cells derived from a living body. As a result, a lack of donors represents a serious problem for these therapies. Furthermore post-transplantation rejection and tissue loss in donors are also serious problems to be solved for the application of these therapies.

Recently these problems have resulted in considerable attention being given to cell transplantation methods using embryonic stem cells (hereafter "ES cells") as one of the therapeutic methods replacing organ transplantation. ES cells are cells established from blastocysts of a fertilized ovum and it is considered possible to induce such cells to differentiate into the various functional cells constituting an individual. Furthermore at the ES cell stage, cell surface antigen related to rejection can be modified. Consequently the efficient differentiation of ES cells into hepatocytes for use in cell transplantation is expected to solve various problems related to transplantation therapies such as donor shortage, rejection and tissue loss in the organ donor.

DISCLOSURE OF THE INVENTION

In view of the above problems, this invention has the object of providing an agent for promoting differentiation of an ES cell, or preferably an agent for promoting differentiation of an ES cell into a hepatocyte, or a prophylactic agent for teratoma.

In another aspect, it is an object of this invention to provide a method of promoting differentiation of an ES cell, or preferably a method of promoting differentiation of an ES cell into a hepatocyte, or a method of preparing a hepatocyte.

In yet another aspect, it is an object of this invention to provide a method of transplanting hepatocytes or a method of preventing teratoma.

As a result of active research into solving the above problems, the present inventors have attempted to find a method for efficiently inducing the differentiation of an ES cell into a hepatocyte. As result, the inventors have clarified for the first time that urokinase-type plasminogen activator (hereafter uPA) induces efficiently the differentiation of ES cells into hepatocytes, and have completed the present invention.

In other words, the invention is as follows.
(1) An agent for promoting differentiation of an ES cell, the agent comprising urokinase-type plasminogen activator.
(2) An agent for promoting differentiation of an ES cell into a hepatocyte, the agent comprising urokinase-type plasminogen activator.
(3) A prophylactic agent for teratoma, the agent comprising urokinase-type plasminogen activator.
(4) A method of promoting differentiation of an ES cell comprising the step of contacting urokinase-type plasminogen activator with the ES cell.
(5) A method of promoting differentiation of an ES cell into a hepatocyte comprising the step of contacting urokinase-type plasminogen activator with the ES cell.
(6) A method of preparing a hepatocyte comprising the step of contacting urokinase-type plasminogen activator with an ES cell to differentiate the ES cell into a hepatocyte.

This invention also relates to the following.
(7) A method of transplanting hepatocytes comprising the step of contacting urokinase-type plasminogen activator with an ES cell and transplanting the hepatocyte differentiated from the ES cell into a living body.
(8) A method of preventing teratoma comprising the step of contacting urokinase-type plasminogen activator with an ES cell and transplanting the hepatocyte differentiated from the ES cell into a living body.

This invention provides an agent for effectively promoting differentiation of an ES cell, or preferably an agent for promoting differentiation of an ES cell into a hepatocyte, or a prophylactic agent for teratoma. The agents comprise uPA. Furthermore this invention provides a method of promoting differentiation of an ES cell, or preferably a method of promoting differentiation of an ES cell into a hepatocyte or a method of preparing a hepatocyte. This invention also provides a method of transplanting hepatocytes with low probability of developing teratoma. Furthermore this invention also provides a method of preventing teratoma.

This invention discloses for the first time that uPA induces differentiation of ES cells into hepatocytes and that uPA can be used for the efficient differentiation of ES cells into hepatocytes.

This invention may preferably provide a solution for various problems related to transplantation therapies such as lack of donors, immunological rejection or tissue loss in organ donor.

Furthermore the hepatocytes obtained using this invention are preferably more highly differentiated than cells obtained using conventional methods of inducing differentiation. Consequently this invention preferably provides hepatocytes which are more adapted for transplantation therapies with low risk of developing teratoma (teratoid tumors) caused by transplantation.

BRIEF DESCRIPTION OF DRAWINGS

The patent or application file contains at least one drawing executed in color. Copies of this patent or patent application publication with color drawing(s) will be provided by the office upon request and payment of the necessary fee.

FIG. 3 shows uptake of indocyanine green by a cell after differentiation-inducing culturing.

FIG. 7 shows the effect of p-aminobenzamidine on the differentiation of ES cells into hepatocytes.

FIG. 14 shows a method of transplanting the differentiated cells originating from ES cells into mouse via the spleen.

BEST MODE FOR CARRYING OUT INVENTION

Figure 1:
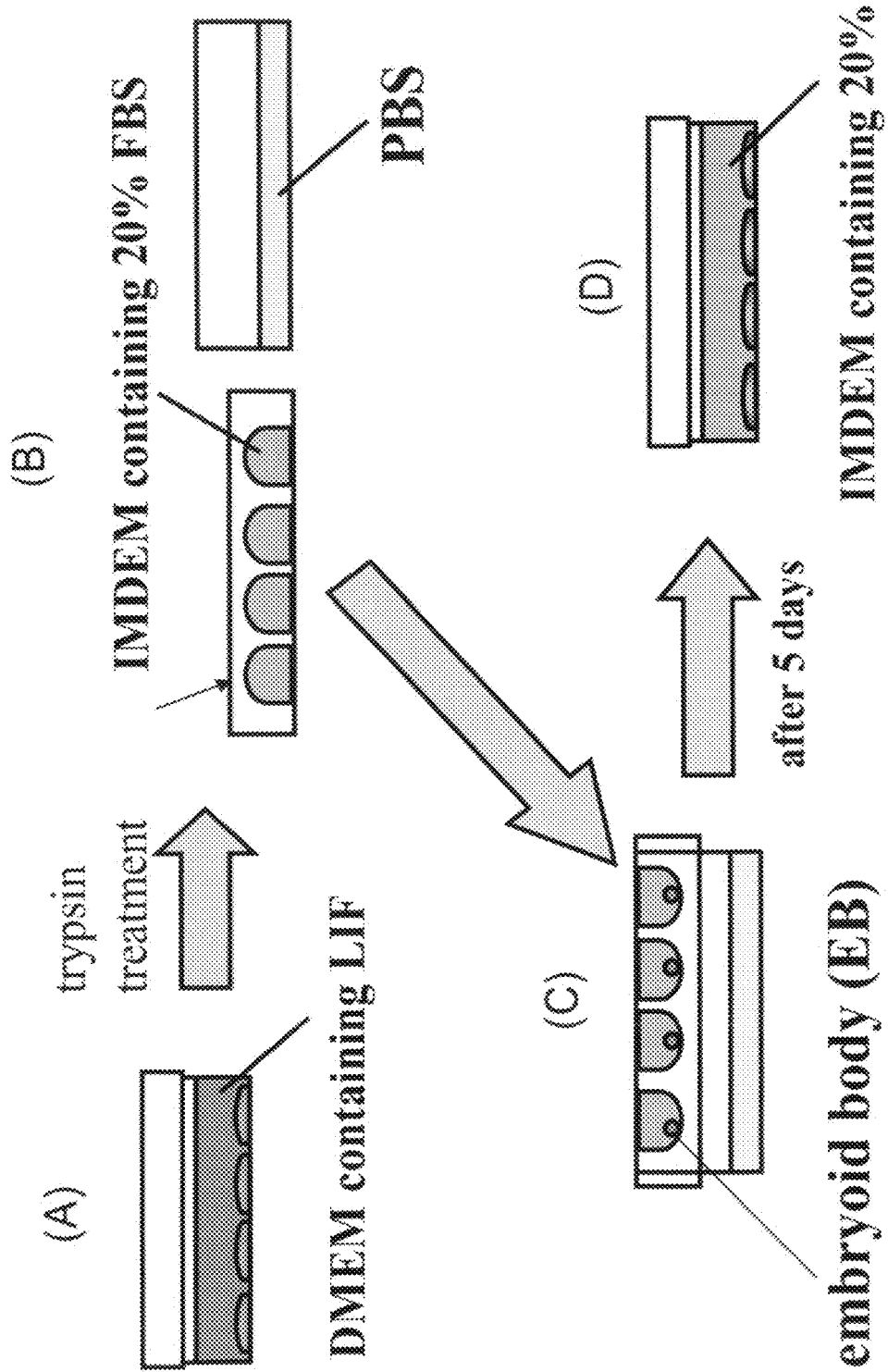
FIG. 1 shows a method of inducing differentiation and a method of forming an embryoid body using a hanging drop method.

The invention will be described in detail hereafter. The following embodiments of the invention are examples for the purpose of describing the invention and are not for the purpose of limiting the invention to the form of the embodiments.

Publications cited in the present specification are incorporated by reference into the present specification in their entirety.

1. Overview

This invention relates to the effect of uPA in promoting differentiation of ES cells and has been completed based on the fact that when ES cells are differentiated in the presence of uPA, the ES cells are efficiently differentiated into hepatocytes. The hepatocytes obtained in this invention are characterized by being more highly differentiated than hepatocytes differentiated by conventional methods which do not use uPA. Consequently this invention has the aspect of potentially preventing from developing teratomas which are an adverse side-effect of cell transplantation.

2. ES Cells

Embryonic stem cells (ES cells) are cultured cells isolated from the inner cell mass (ICM) of five- or six-day blastocysts after fertilization. An ES cell can be proliferated by culturing, and since the ES cell is obtained at an initial embryonic stage, it has a quality (pluripotency) of being able to develop into any of the cells constituting a living body.

Although there is no particular limitation on the origin of the ES cell, it is preferred to use cells of the same type as the recipient. For example, when hepatocytes prepared by a method of this invention are transplanted into a human subject, it is preferred that the ES cells to be used are those of human origin.

When the ES cell is an ES cell established by an allogenic cross, it is preferred that any of the lines used in the cross are the same lines as the recipient.

When ES cells originate from a gender which is different to the gender of the recipient and then are differentiated and transplanted as differentiated cells of ES cell origin, the level of implantation of the transplanted cells can be confirmed by examining the expression of the sex determining markers in the organs of the recipient.

The ES cells used in this invention include, but not limited to, TT2 cells. TT2 cells are a line of ES cells originating from male mice established by crossing C57/BL6 mouse (female) with CBA mouse (male) (Yagi T et al., Anal Biochem 1993 October; 214(1):70-6.). TT2 cells can be produced by developing four day embryos obtained by crossing C57/BL6 mouse with CBA mouse on a feeder cell layer and establishing the line by passaging the resulting inner cell mass several times on feeder cells. Thus this invention allows the use of C57/BL6 mouse or preferably C57/BL6 female mouse in a recipient receiving transplanted differentiated cells of TT2 origin.

ES cells can be cultured (including passaging) by the conventional methods. A person of normal skill in the art can set appropriate culturing conditions. For example, ES cells can be cultured by methods described in the examples.

During culturing, the culture media can be supplemented with additives in order to suppress differentiation of the ES cells. For example, ES cells can be cultured in the presence of LIF (leukemia inhibitory factor).

Furthermore ES cells can be maintained in an undifferentiated state by using feeder cells in combination with LIF.

ES cells are differentiated by firstly forming an embryoid body (hereafter EB) from an ES cell.

Hanging drop method and agarose method are known as a method for the formation of an EB. However a person of normal skill in the art can perform the process using known methods. For example, an EB can be formed using a method described in the example.

Alternatively an EB can be formed from an ES cells using ultra low-attachment culturing equipment.

3. Urokinase-Type Plasminogen Activator (uPA)

Urokinase-type plasminogen activator (uPA) (sometimes simply referred to as "urokinase") is a protein (high-molecular weight type) with a molecular weight of approximately 54 kD which is known as an enzyme in the fibrinolytic system.

In addition to the above activated (double-stranded) high-molecular weight type of uPA, it is known that there also exists a low-molecular weight type of uPA with a molecular weight of 31 kD which is constituted by a residual portion of the high-molecular weight type. The low-molecular weight type of uPA is a polypeptide fragment containing the active domain of the high-molecular weight type of uPA. Furthermore uPA is known to exist as an inactive (single-chain) precursor pro-uPA (molecular weight approximately 54 kD). Any of this high-molecular weight type of uPA, low-molecular weight type of uPA and precursor pro-uPA may be used as uPA in this invention.

There is no particular limitation on the origin of uPA used in this invention and uPA originating from any type can be used.

In this invention, the uPA contains a protein comprising an amino acid sequence which is the same or substantially the same as the amino acid sequence shown in SEQ. ID No. 2, or preferably a protein consisting of an amino acid sequence which is the same or substantially the same as the amino acid sequence shown in SEQ. ID No. 2. uPA consisting of the amino acid sequence shown in SEQ. ID No. 2 is high-molecular weight type of uPA of human origin. The amino acid sequence shown in SEQ. ID No. 2 is registered in GenBank as accession numbers NP_002649 and NM_002658.

"An amino acid sequence which is substantially the same as the amino acid sequence shown in SEQ. ID No. 2" as used herein includes an amino acid sequence which has substantially 80% or more, preferably 90% or more, yet more preferably 95% or more, or most preferably 98% or more homology (identity) with the an amino acid sequence shown in SEQ. ID No. 2 and a polypeptide of which has an action to promote differentiation of ES cells.

In addition to the amino acid sequences above, "an amino acid sequence which is substantially the same as the amino acid sequence shown in SEQ. ID No. 2" also includes the amino acid sequence shown in SEQ. ID No. 2 wherein one or more amino acids are deleted, substituted or added and which the amino acid sequence is an amino acid sequence of a polypeptide having an action to promote differentiation of ES cells.

In this invention, "an action to promote differentiation of ES cells" means an action to promote differentiation of ES cells or preferably an action to promote differentiation of ES cells into hepatocytes. Furthermore in this invention, "having an action to promote differentiation of ES cells" means that a comparison with control cells not treated with the polypeptide shows that the polypeptide has an action of increasing the rate of differentiation of ES cells, an action of increasing the number or proportion of differentiated cells (action of increasing the level of differentiation) or an action of increasing the level of differentiation and maturation of ES cells.

A method of measuring an action to promote differentiation of ES cells is described hereafter.

An amino acid sequence shown in SEQ. ID No. 2 wherein one or more amino acids are deleted, substituted or added includes (i) an amino acid sequence wherein 1-10 (preferably 1-5, more preferably 1-3, yet more preferably 1-2, most preferably 1) amino acids are deleted from the amino acid sequence shown in SEQ. ID No. 2, (ii) an amino acid sequence wherein 1-10 (preferably 1-5, more preferably 1-3, yet more preferably 1-2, most preferably 1) amino acids are substituted by other amino acids in the amino acid sequence shown in SEQ. ID No. 2, (iii) an amino acid sequence wherein 1-10 (preferably 1-5, more preferably 1-3, yet more preferably 1-2, most preferably 1) amino acids are added to the amino acid sequence shown in SEQ. ID No. 2, (iv) an amino acid sequence wherein 1-10 (preferably 1-5, more preferably 1-3, yet more preferably 1-2, most preferably 1) amino acids are inserted into the amino acid sequence shown in SEQ. ID No. 2, or (v) an amino acid sequence resulting from a combination of (i) to (iv) above.

Furthermore uPA used in this invention, as long as it has an action to promote differentiation of ES cells, may be in the form of a fusion protein with alkaline phosphatase (AP), glutathione-S-transferase (GST), maltose binding protein (MBP) or the like.

In this invention, uPA contains a polypeptide encoded by a DNA having a base sequence which is the same or substantially the same as the base sequence shown in SEQ. ID No. 1, or preferably a polypeptide encoded by a DNA consisting of a base sequence which is the same or substantially the same as the base sequence shown in SEQ. ID No. 1. The DNA consisting of the base sequence shown in SEQ. ID No. 1 is a DNA encoding high-molecular weight type of uPA of human origin. The base sequence shown in SEQ. ID No. 1 is registered in Genbank as accession number NM_002658.

"A base sequence which is substantially the same as the base sequence shown in SEQ. ID No. 1" includes a base sequence having substantially 80% or more, preferably 90% or more, yet more preferably 95% or more, or most preferably 98% or more homology (identity) with the base sequence shown in SEQ. ID No. 1.

"A base sequence which is substantially the same as the base sequence shown in SEQ. ID No. 1" in addition to the base sequences above also includes the base sequence shown in SEQ. ID No. 1 wherein one or more bases are deleted, substituted or added and which the base sequence is a base sequence encoding a polypeptide having an action to promote differentiation of ES cells.

A base sequence shown in SEQ. ID No. 1 wherein one or more bases are deleted, substituted or added includes (i) a base sequence wherein 1-10 (preferably 1-5, more preferably 1-3, yet more preferably 1-2, most preferably 1) bases are deleted from the base sequence shown in SEQ. ID No. 1, (ii) a base sequence wherein 1-10 (preferably 1-5, more preferably 1-3, yet more preferably 1-2, most preferably 1) bases are substituted by other bases in the base sequence shown in SEQ. ID No. 1, (iii) a base sequence wherein 1-10 (preferably 1-5, more preferably 1-3, yet more preferably 1-2, most preferably 1) bases are added to the base sequence shown in SEQ. ID No. 1, (iv) a base sequence wherein 1-10 (preferably 1-5, more preferably 1-3, yet more preferably 1-2, most preferably 1) bases are inserted into the base sequence shown in SEQ. ID No. 2, or (v) a base sequence resulting from a combination of (i) to (iv) above.

Mutations in DNA may be introduced by known methods such as the Kunkel method or Gapped duplex method using a mutation introducing kit that utilizes the site-directed mutagenesis, such as the QuikChange™ Site-Directed Mutagenesis Kit (Stratagene), GeneTailor™ Site-Directed Mutagenesis System (Invitrogen), TaKaRa Site-Directed Mutagenesis System (Mutan-K, Mutan-Super Express Km, or the like: TaKaRa Biotechnology).

A base sequence which is substantially the same as the base sequence shown in SEQ. ID No. 1 includes a base sequence of a DNA encoding a polypeptide having an action to promote differentiation of ES cells where the DNA hybridizes under stringent conditions with a DNA comprising a base sequence complementary to the DNA consisting of the base sequence shown in SEQ. ID No. 1.

Herein "stringent conditions" means for example "5×SSC, 0.1% SDS, 42° C.", "1×SSC, 0.1% SDS, 50° C." or "2×SSC, 0.1% SDS, 37° C.", and "more stringent conditions" means for example "1×SSC, 0.1% SDS, 65° C.", "0.5×SSC, 0.1% SDS, 50° C." or "0.1×SSC, 0.1% SDS, 55° C.". Reference may be made to Molecular Cloning, A Laboratory Manual 2nd ed. (Cold Spring Harbor Laboratory Press (1989)) for details of procedures for methods of hybridization.

In this invention, low-molecular weight type of uPA contains a protein comprising an amino acid sequence which is the same or substantially the same as an amino acid sequence at positions 156-431 in SEQ. ID No. 2. Furthermore in this invention, low-molecular weight type of uPA contains a protein encoded by a DNA comprising a base sequence which is the same or substantially the same as the base sequence at positions 466-1293 in SEQ. ID No. 1.

Precursor, pro-uPA can be converted into active uPA by cleaving into a two-chain form using plasmin or kallikrein. In this invention, precursor, pro-uPA can promote differentiation of ES cells after conversion into active uPA.

In this invention, uPA may originate in any living organism. For example, it is known that urine contains uPA and therefore uPA isolated from urine using known methods may be used. Furthermore cells expressing uPA may be disrupted, and uPA to be used may be isolated from the homogenate using known methods. Known methods include for example various methods of chromatography such as gel filtration chromatography, affinity chromatography, ion exchange chromatography and high-performance liquid chromatography, ammonium sulfate precipitation methods and dialysis. A person of normal skill in the art may select one or a plurality of known methods as required.

In this invention, commercially purchased uPA may be used and may be obtained for example as urokinase (Benesis-Mitsubishi Pharma Corp.), urokinase (Mochida Pharmaceutical Co., Ltd.), urokinase (Nihon Pharmaceutical Co., Ltd.-Takeda Pharmaceutical Company Ltd., Wakamoto Pharmaceutical Co., Ltd.-Fujisawa Pharmaceutical Co., Ltd., Kowa Company Ltd.).

In this invention, uPA may be used without modification or may be used as a prepared pharmaceutical composition. There is no particular limitation on the pharmaceutical composition as long as is contains uPA. A pharmaceutical composition according to this invention includes various preparations containing uPA such as oral preparations: pills, powdered medicines, fine grain agents, granules, capsules and syrups and parenteral agents: suppositories, injectable solutions, ointments and adhesive skin patches. A person of normal skill in the art can prepare uPA using known methods.

In this specification, the concentration of a solution containing uPA can be expressed as an uPA activity per unit solution (for example, u/mL). uPA activity can be expressed as enzymatic activity measured using a method determining international units.

uPA activity can be measured using a chromogenic synthetic substrate, S-2444, or a fibrin plate.

As shown in the examples hereafter, uPA which is a type of fibrinolytic factors has an action of promoting differentiation of ES cells into hepatocytes. tPA of tissue origin has no effect on differentiation of an ES cell into a hepatocyte. Experiments using various types of inhibitors have shown that there is a high possibility that the action of promoting differentiation of ES cells by uPA results from the activity of uPA.

4. Method of Promoting Differentiation of ES Cells

In this invention, uPA can promote differentiation of ES cells. Preferably, uPA in this invention promotes differentiation of an ES cell into a hepatocyte.

In this invention, as described supra, ES cells may form an embryoid body. Thereafter differentiation can be induced or differentiation is possible without the formation of an embryoid body (EB).

An ES cell can be differentiated by culturing in ma culture medium not containing differentiation inhibiting factors such as LIF. For example, ES cells can be differentiated by culturing in a culture medium (for example, IMDM containing 20% FBS) not containing LIF.

When inducing differentiation of ES cells which have been formed an EB, for example, it is possible to induce their differentiation by inoculating the EB on a collagen-coated dish, at 72-168 hours after commencement of hanging drop-culturing, and then culturing using IMDM containing 20% FBS. Commercially available collagen-coated dishes (for example, Iwaki, code# 4010-010) may be used or the dishes may be prepared using known methods.

In this invention, after inoculating the EBs on collagen-coated dish, the culturing medium is supplemented with uPA to a final concentration of 0.1-1000 u/mL, preferably 1-100 u/mL, more preferably 5-50 u/mL, or most preferably 10 u/mL and brought into contact with the ES cells.

Conditions under which ES cells brought into contact with uPA may be suitably selected by a person of normal skill in the art and for example, contact may be effected in an incubator at 37° C., under 5% $CO_2$ for 1-30 days, preferably 5-25 days, more preferably 10-20 days, and most preferably 15 days. Differentiation of ES cells, or preferably differentiation of ES cells into hepatocytes can be promoted by bringing ES cells into contact with uPA.

In this invention, the action of uPA in promoting differentiation of ES cells or the course of differentiation of ES cells can be determined by measuring the level of expression of a differentiation marker or by observing the morphology using an optical microscope.

Measurements of the level of expression of the known differentiation markers can be used in order to evaluate the course of ES cell differentiation such as the types of cell resulting from ES cell differentiation, the differentiation time and the amount of differentiated cells. For example, octmer binding protein-4 (Oct-4) is an example of a marker for undifferentiated cells, cytokeratin19 (CK-19) is a differentiation marker in the bile duct system, albumin (A1b), α-fetoprotein (AFP) (embryonic-stage cell), cytochrome P450 7A1 (Cyp7a1), $α_1$-anti-trypsin (AAT), transthyretin (TTR) are differentiation markers for hepatocyte and cardiac muscle actin (CMA) is a differentiation marker gene for differentiation of the cardiac muscle mesoderm. Consequently if the expression of A1b is confirmed for example, there is a strong possibility that that cell has differentiated into a hepatocyte.

Sex determining markers such as sex-determining region Y gene (SRY) may be used in order to determine the implantation of ES cells.

The level of the expression of the sex-determining markers or the differentiation markers can be analyzed by measuring the amount of protein or the amount of mRNA expressed in a cell.

The measurement of mRNA can be performed using methods such as RT-PCR, real time PCR, DNA microarrays, northern blot, in situ hybridization, and preferably it is performed using RT-PCR. A person of normal skill in the art can carry out the above methods according to conventional protocols. In these measurements, a housekeeping gene such as glyceraldehyde-3-phosphate dehydrogenase (GAPDH) can be used as a reference gene.

The measurement of protein can be performed using immunochemical methods such as immunohistochemical techniques, immunoprecipitation methods, Western blotting, flow cytometry or fluorescence activated cell sorting (FACS), ELISA or RIA, or by methods such as mass spectrometry. Preferably, measurement may be performed using Western blotting. The above methods can be performed in accordance with a conventional protocol.

Differentiation into hepatocytes can be confirmed by staining glycogen storage cells using PAS staining. A cell which has differentiated into a hepatocyte displays a dark color in PAS staining. Differentiation into hepatocytes can also be confirmed using FACS analysis or immunohistochemical staining using anti-albumin antibodies. These methods can be carried out by known methods such as the methods used in the examples.

Urea synthesis capability can be measured by diacetyl mono oxime methods and it may be used as an indicator of the differentiated function of hepatocytes. For example, cells are washed and then incubated for 2 hours at 37° C. in Hank's medium containing 5 mM $NH_4Cl$. Then the culture solution is collected and the amount of synthesized urea contained in the culture solution can be quantified.

As discussed supra, differentiation of ES cells can be promoted or preferably, the differentiation of ES cells into hepatocytes can be promoted by bringing the ES cells into contact with uPA. This invention provides a method of preparing hepatocytes since hepatocytes can be prepared by differentiating ES cells brought into contact with uPA or by retrieving differentiated hepatocytes. Furthermore this invention provides a novel use of uPA, that is to say, an agent for promoting differentiation of ES cells, or preferably an agent for promoting the differentiation of ES cells into hepatocytes since uPA promotes the differentiation of ES cells or preferably promotes the differentiation of ES cells into hepatocytes.

A group of hepatocytes prepared in accordance with this invention has a lower proportion of undifferentiated cells (higher level of differentiation) than a group of cells prepared using conventional methods of differentiating ES cells without use of uPA.

ES cells have the capacity to differentiate into any cell type when cultured in the presence of defined substances inducing differentiation. Furthermore it is possible to propagate cells without limit in an undifferentiated state by culturing in the presence of a substance inhibiting differentiation. Consequently ES cells are expected to be new sources of cells for cell transplantation therapies. However, even if the differentiation into a specific cell type can be induced, there is no certainty that the specific cell type can be used in cell transplantation. This is due to the fact that there is a possibility of teratoma formation when groups of cells used in transplantation contain undifferentiated cells. A teratoma is a teratoid tumor formed by differentiation from a germ cell.

This invention provides methods of prevention or inhibition of teratoma with uPA and methods of transplantation of hepatocytes having a lower probability of developing teratoma, with uPA.

In the examples described hereafter, cell transplantation was performed using differentiated cells of ES cell origin which were cultured for 18 days to induce differentiation by (a) adding uPA or (b) not adding uPA or using (c) ES cells maintained in an undifferentiated state by not culturing to induce differentiation. When the cells (b) or the cells (c) were transplanted into a mouse, teratomas had been formed in every mouse undergoing transplantation. The expression of Oct-4 which is a marker for undifferentiated cells was confirmed in the liver forming teratoma. Thus it is conceivable that teratoma formation resulted from a higher proportion of more undifferentiated cells being present among cells induced into differentiating without using uPA and those cells subsequently differentiating into various cells in the implanted organ. On the other hand, mice undergoing transplantation of cells (a) induced to differentiate by adding uPA did not develop teratoma. These results show that when differentiation is induced by the addition of uPA, there is a lower probability of teratoma formation when performing cell transplantation.

In other words, ES cells form teratoma when there are a large residual number of undifferentiated cells. However it is clear that the addition of uPA increases the level of differentiation and may reduce the probability of teratoma formation or prevent or inhibit development of teratoma. "Prevent" as used in this invention means reducing the probability of development of teratoma in comparison to conventional methods of transplantation not using uPA, delaying the development of teratoma or inhibiting the development of teratoma.

Consequently this invention provides an agent for reducing the probability of development of teratoma or a prophylactic agent for teratoma, which the agent comprises uPA. Furthermore this invention provides methods of transplantation of hepatocytes, methods of reducing the probability of development of teratoma or methods of preventing or inhibiting the development of teratoma, comprising the transplantation of hepatocytes which have differentiated from ES cells as a result of the ES cells being brought into contact with uPA (differentiated cells of ES cell origin) into a living body.

There is no particular limitation on the living body (recipient) into which the cell is transplanted, however it is preferred that it is a mammal. Mammals include for example, mice, rats, guinea pigs, hamsters, rabbits, dogs, cats, pigs, sheep, goats, horses, cows, monkeys or humans. It is preferred that the mammal is a human or a mouse.

Methods of cell transplantation include known methods such as transplantation via the spleen or intraportal infusion.

EXAMPLES

The invention will be described in further detail hereafter with the examples. However the invention is not limited to the following examples.

Methods

1. Culturing of ES Cells and Inducing Differentiation to Hepatocytes (1) Method of Culturing ES Cells In the examples hereafter, experiments were carried out using TT2 ES cells from mice as a model cell.

Firstly a dish (hereafter gelatin coated dish) was prepared by placing 8 mL of PBS (−), in which gelatin (Nacalai tesque, Code# 16631-05) was dissolved to a concentration of 0.1%, into a 100 mm tissue culture dish (Falcon, Code# 35-3002) and allowing to stand for three hours or more. TT2 cells were cultured on the gelatin-coated dish. Culturing was carried out using Dulbecco's modified Eagle's medium (DMEM; Nissui Pharmaceutical Co., Ltd., Code# 05915) supplemented with the substances below (hereafter "ES cell culturing medium" or "ESM"). The cells were cultured until confluence at 37° C., under an atmosphere of 5% $CO_2$/95% air (Heath and Smith, J Cell Sci Suppl. 1988; 10:257-66.).

Substances Added to DMEM

Inactivated 20% fetal bovine serum (FBS; Bio west, Lot# S05115S1820, Code# S1820)

1.5 mg/mL sodium hydrogen carbonate (Nacalai tesque, Code# 168-06)

20 mM D-(+)-glucose (Nacalai tesque, Code# 31213-15)

25 mM HEPES (Nacalai tesque, Code# 175-14)

1000 U/mL recombinant mouse leukemia inhibitory factor (LIF; Amrad, Code# 539-24301)

100 µM 2-mercaptoethanol (2-ME; Nacalai tesque, Code# 214-18)

10 mM non-essential amino acids for MEM (NEAA; sigma, Code# M-7145)

(2) Method of Thawing ES Cells

TT2 cells cryopreserved in liquid nitrogen in a cryotube were rapidly thawed in a water bath at 37° C., immediately transferred to a centrifuge tube containing ESM and suspended. After centrifuging (1000 rpm, 4° C., 5 min), the supernatant was removed. This operation was repeated twice to wash the cells. After washing the cells, the cells were suspended again in ESM and used to inoculate a 100 mm gelatin coated dish. Unadhered cells were removed after 24 hours and thereafter the ES cells were cultured until confluence exchanging the culture medium every 72 hours.

(3) Method of Passaging ES Cells

After the cells reached confluence, the culture medium was removed and the cells were washed in PBS (−). A 0.25% Trypsin-EDTA solution (0.25% trypsin, 0.1 M EDTA-2Na-PBS) was added and incubation performed for 1-2 minutes in a $CO_2$ incubator and then the cells were detached from the dish surface. ESM was added and after stopping enzymatic reactions, the cellular suspension was collected and placed into a centrifuge tube and centrifuged (1000 rpm, 4° C., 5 min). The supernatant was removed after separation. The cells were suspended again in ESM and used to inoculate a 10 cm gelatin coated dish with a cellular density of $1.7 \times 10^6$ cells/100 mm dish. Thereafter the cells were cultured until confluence exchanging the culture medium every 72 hours.

(4) Method of Storage of ES Cells

ES cells were detached from the dish using a 0.25% trypsin-EDTA solution (0.25% trypsin, 0.1 M EDTA-2Na-PBS). The cells were collected and suspended at a cellular density of 6.0×10⁶ cells/mL in ESM containing 10% dimethyl sulfoxide and separated into 1 mL aliquots in a cryotube. The tube was inserted into a container made of polystyrene foam so that the temperature of the liquid would decrease by 1° C. per one minute. The tube was placed in a freezer at −80° C. and transferred for storage in liquid nitrogen after 24 hours.

(5) Method of Forming Embryoid Body (EB) from ES Cell Using Hanging Prop Method

Figure 2:
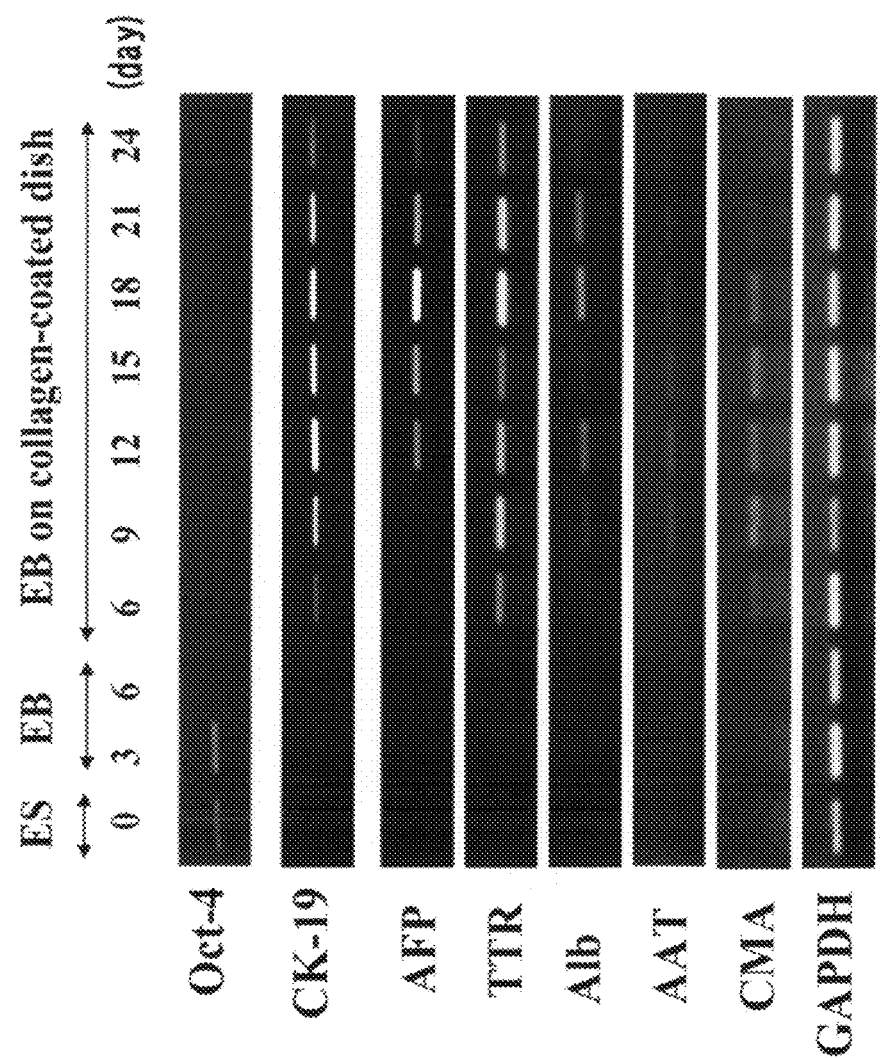
FIG. 2 shows expression of the differentiation markers in an ES cell induced to differentiate by a hanging drop method.
Figure 8:
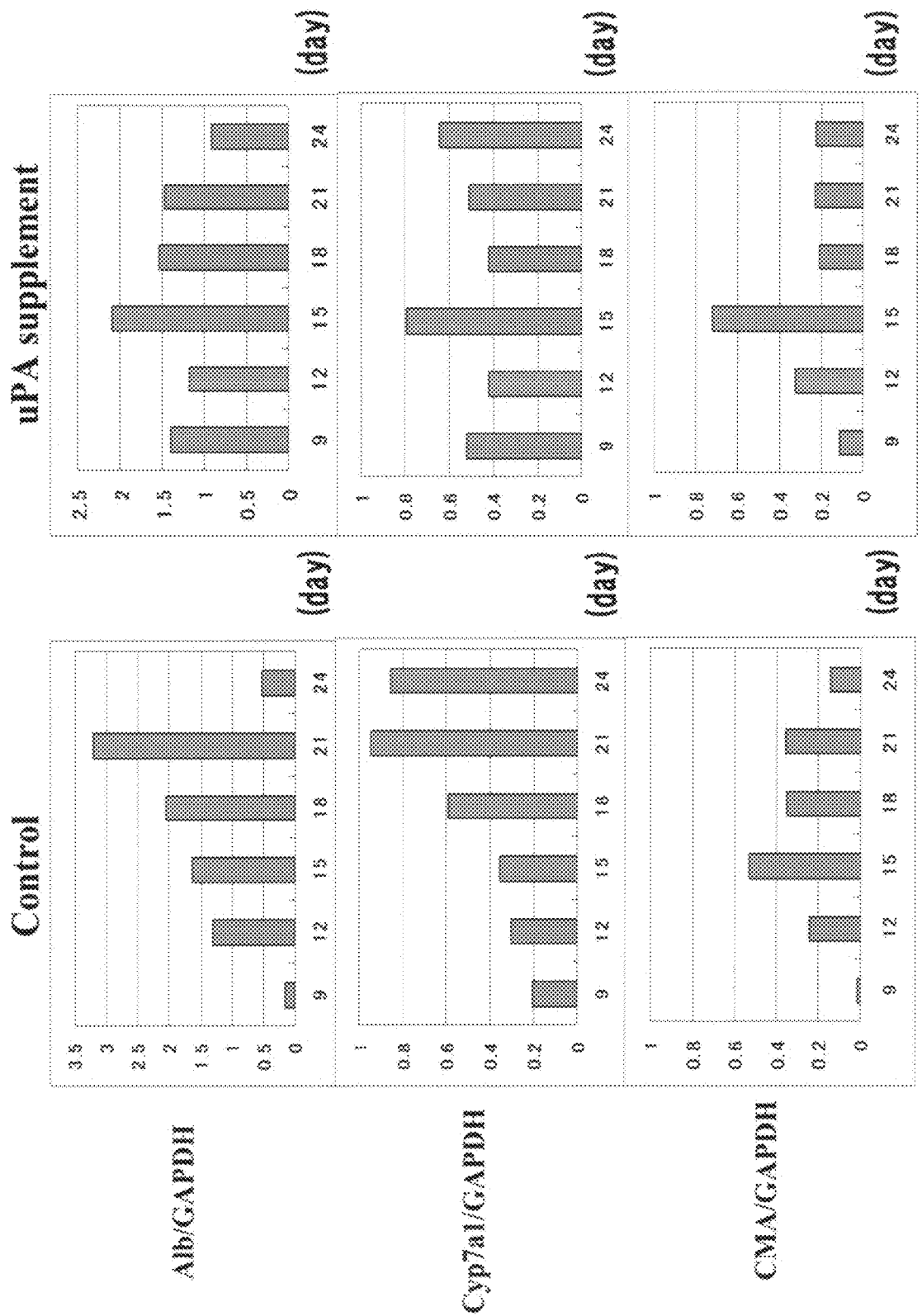
FIG. 8 shows the time course of the gene expressions resulting from supplementation with uPA.
Figure 13:
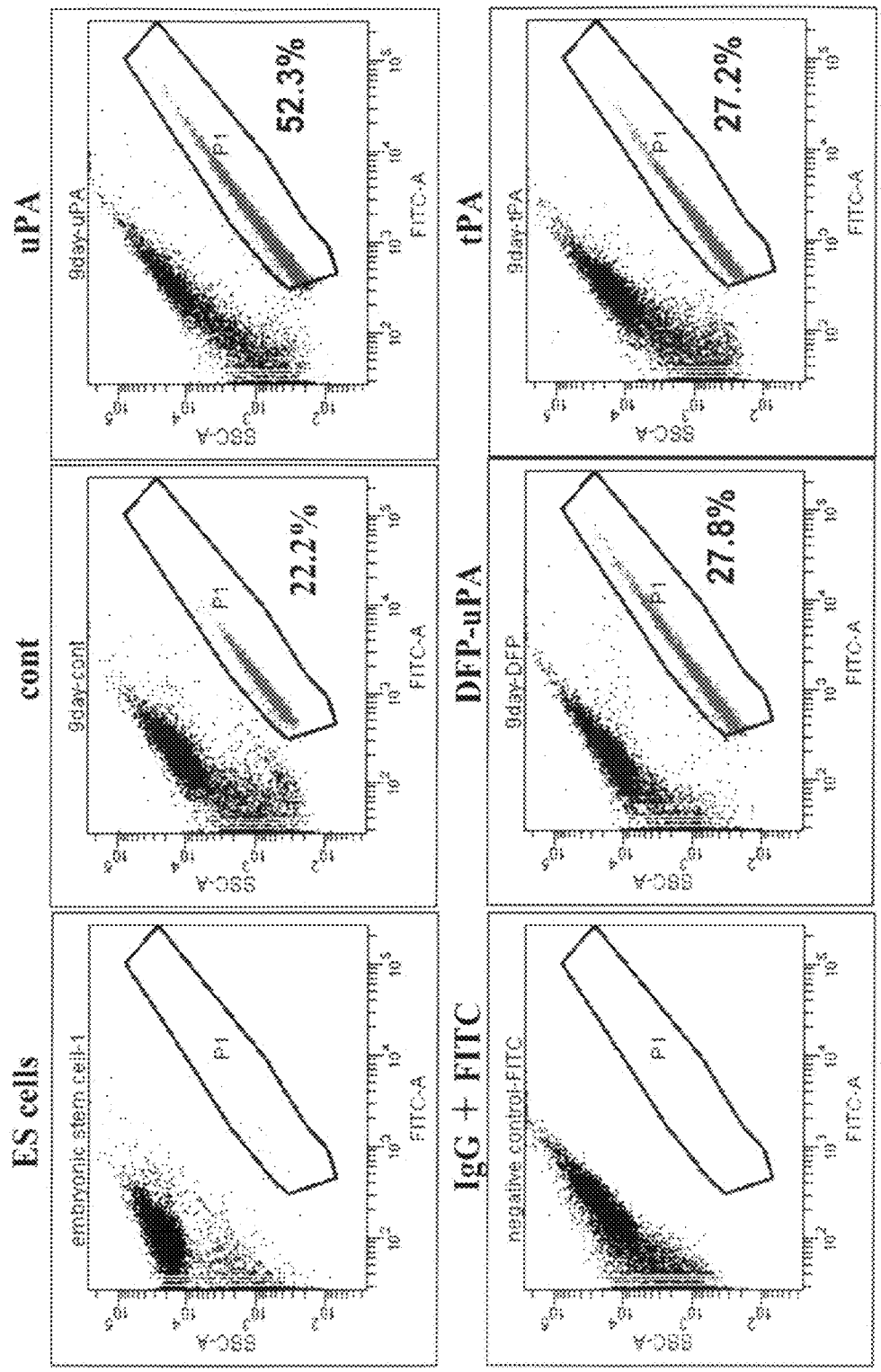
FIG. 13 shows the result of FACS analysis of cells induced their differentiation due to supplementation with uPA, DFP-treated uPA and tPA.

The culture medium was exchanged for Iscove's modified Dulbecco's medium (IMDM) supplemented with FBS, sodium hydrogen carbonate, 2-ME and not supplemented with LIF to induce differentiation (hereafter "IMDM containing 20% FBS") and an EB was formed by a hanging drop method. More precisely, as shown in FIG. 1, (A) cells cultured without differentiation were washed in PBS (−) and separated with trypsin treatment and (B)(C) the separated cells were suspended in IMDM containing 20% FBS, the lid of a 100 mm petri dish (Falcon, Code# 35-1005) was inoculated so that the cell density in a 30 μL drop was 1×10³ cells, the dish section was filled with a phosphate-buffer saline (PBS(−); Nissui Pharmaceutical Co., Ltd., Code# 5913) to prevent drying out and the cells were cultured for five days. (D) A resulting EB in the hanging drop was transferred to a 60 mm collagen-coated dish (Iwaki, Code# 4010-010) on the fifth day after the drop formation, attached to the dish and cultured to induce differentiation in IMDM containing 20% FBS. Hereafter "IMDM containing 20% FBS" will be referred to as "differentiation-inducing medium". The number of days of culturing shown in FIGS. 2, 8 and 13 shows the number of days after commencement of culturing using a hanging drop method.

In this examples, the level of differentiation of cells of EB origin formed using a hanging drop method was determined from the observed morphology using an optical microscope, or from the level of expression of mRNA of a differentiation marker or protein thereof. For example, after purifying the total RNA from the cells using Isogen™ (NipponGene), the expression of various types of the marker genes was examined using RT-PCR. The amount of protein expression was examined using Western blot analysis. These methods are described hereafter.

2. Analysis of mRNA Expression of Various Differentiation Markers Using Reverse Transcriptase-Polymerase Chain Reaction (RT-PCR)

The culture solution was removed and the cells were washed twice in PBS (−), 1 mL of Isogen™ (NipponGene, Code#311-02501) was added to a 60 mm dish, allowed to stand for 5 minutes, then the cells were harvested using a cell scraper. 0.2 mL of chloroform (Nacalai tesque, Code# 08402-55) was added to the resulting solution, the solution was stirred for 15 seconds and allowed to stand at ambient temperature for 3 minutes. After centrifuging (12000 rpm, 15 minutes, 4° C.), the supernatant was recovered. 0.5 mL of 2-propanol was added to the resulting supernatant, and the supernatant was reverse stirred, allowed to stand for 5 minutes at ambient temperature, centrifuged (12000 rpm, 10 minutes, 4° C.) again and the supernatant removed. The resulting precipitant was washed in 1 mL of 70% ethanol and centrifuged (7500 rpm, 5 minutes, 4° C.). The precipitant was allowed to dry naturally at ambient temperature. Thereafter it was dissolved in 50 μL of autoclaved ultrapure water (DW) to obtain total RNA.

The prepared total RNA was diluted 100 times in DW and quantified using a UV method (RNA; O.D.260=40 μg/mL; 1.0). A certain amount of the total RNA was subjected to RT-PCR. PCR reactions were performed using a Gene Amp PCR System 9700 (Applied Biosystems, Norwalk, USA). Conditions for PCR and primers are described below.

After synthesizing a first strand of cDNA in 5 μL or less of a reaction solution containing 0.25 μg of total RNA, PCR was performed using a thermocycler (GeneAmp PCR System 9700, Perkin-Elmer, Calif., USA). PCR used Taq DNA polymerase (NipponGene, Code# 317-04161). cDNA was amplified in a single cycle by denaturation of cDNA (94° C., 1 minute), annealing reaction (optimal temperature for each primer shown below, 1 minute), extension reaction (72° C., 1 minute) for a fixed number of cycles.

Composition of the Reaction Solution

5× Reaction Buffer (Wako Pure Chemicals, Code# 186-01251) 1 μL

10 μmol/1 L Primer 0.25 μL, 10 mM dNTPs (Toyobo Co. Ltd., Code# ATP-101, TTP-101, CTP-101, GTP-101) 0.5 μL 10 U/μL RNase inhibitor (Wako Pure Chemicals, Code# 547-00601) 0.25 μL 10 U/μL M-MLV RNase (Wako Pure Chemicals, Code# 186-01251) 0.5 μL total RNA 0.25 μg Primers were designed and synthesized using genetic information from mice. The base sequence of each primer, the annealing temperature and number of cycles are shown below.

```
Transthyretin (TTR)
                                        (SEQ. ID No. 3)
(5'-CGT GGC TGT AAA AGT GTT CA,
                                        (SEQ. ID No. 4)
5'-AGA GTC GTT GGC TGT GAA AA;
55.2° C.; 20 cycles), α-fetoprotein (AFP)
                                        (SEQ. ID No. 5)
(5'-CCC CCA TTC TCT GAG GAT AA,
                                        (SEQ. ID No. 6)
5'-CTT TGG ACC CTC TTC TGT GA;
55.2° C.; 25 cycles), α1-anti-trypsin (AAT)
                                        (SEQ. ID No. 7)
(5'-TGT CCC TCT CTG GAA ACT AT,
                                        (SEQ. ID No. 8)
5'-TGT TGA AGT TCA GGA TAG GG;
54.2° C.; 28 cycles), albumin (Alb)
                                        (SEQ. ID No. 9)
(5'-TTC CTC CTT TGC CTC GCT GGA CTG GTA TTT,
                                        (SEQ. ID No. 10
5'-GCG AAT TCA TGG AAC GGG GAA ATG CCA AGT;
60° C.; 30 cycles), glyceraldehyde-3-phosphate dehydrogenase (GAPDH)
                                        (SEQ. ID No. 11)
(5'-ACC ACA GTC CAT GCC ATC AC;
                                        (SEQ. ID No. 12)
5'-TCC ACC ACC CTG TTG CTG TA;
60° C.; 18 cycles), octmer binding protein-4 (Oct-4)
                                        (SEQ. ID No. 13)
(5'-GGC GTT CTC TTT GGA AAG GTG TTC,
                                        (SEQ. ID No. 14)
5'-CTC GAA CCA CAT CCT TCT CT;
60° C.; 18 cycles),
```

-continued cytokeratin19 (CK-19)
(SEQ. ID No. 15)
(5'-AAG CAG CTC ATG GAC ATC AA;
(SEQ. ID No. 16)
5'-CTT TTA TCA CCC CAG TCA GG;
57.6° C.; 22 cycles), cytochrome P450 7A1 (Cyp7a1)
(SEQ. ID No. 17)
(5'-AGG ACT TCA CTC TAC ACC;
(SEQ. ID No. 18)
5'-GCA GTC GTT ACA TCA TCC;
56° C.; 30 cycles), sex-determining region Y gene (SRY)
(SEQ. ID No. 19)
(5'-CAG TTC CAC GAC CAG CAG CTT ACC TAC;
(SEQ. ID No. 20)
5'-AGC CAG GCA TCT AGT AAG AGT CCT TGA CC;
58° C.; 36 cycles), cardiac muscle actin (CMA)
SEQ. ID No. 21)
(5'-AAA TCA CTG CAC TGG CTC C;
(SEQ. ID No. 22)
5'-TGG GCC TGC CTC ATC ATA C;
56° C.; 23 cycles), urokinase-type plasminogen activator (uPA)
(SEQ. ID No. 23)
(5'-TTC AAT CCC ACA TTG GAG AAG;
(SEQ. ID No. 24)
5'-TCT TTT CAG CTT CTT CCC TC;
58° C.; 25 cycles)

The amplified DNA was subjected to electrophoresis in 1.5% agarose gel with a DNA molecular weight marker (NipponGene, Smart Ladder, Code# 315-00664). Thereafter staining was performed in ultrapure water supplemented with ethidium bromide and the electrophoretic migration image photographed using a Polaroid camera. A scanner was used to perform quantitative analysis of the bands of PCR products using an image analysis software.

3. Measurement of Albumin Expression Level Using Western Blot Analysis.

After removal of the culturing solution, cells at each time point were washed twice in PBS (−). 500 µL of PBS (−) was added to a 60 mm dish and the cells were harvested by detaching using a cell scraper. The cells were disrupted using ultrasonification to obtain samples to be tested. The protein concentration of the samples was measured and adjusted to the lowest protein concentration in comparative samples (1075-1200 µg/mL). An amount of a sample buffer (0.5 M Tris-HCl, 10% SDS, 10% glycerol, 1% bromophenol blue, pH 6.8) equal to the sample was mixed with the sample to prepare the sample for SDS. 15 µL of the sample prepared for SDS was used in the electrophoresis at 8 mA in a polyacrylamide gel with 10% (running gel) and 5% (stacking gel). A filter paper (Whatman, Chromatography Paper, 46×57 cm, 3 mM Chr, Code# 3030-917) and a membrane (Advantec, cellulose nitrate membrane, 220×220 mm 0.45 µm, Code# A045A224D) were soaked in a transfer buffer (20 mM Tris, 150 mM glycine, 20% methanol). Then the membrane along with the filter paper was fitted to a blotting device together with the running gel after electrophoresis, and blotting was performed for 16 hours at 4° C., 30 V, 500 mA and 40 W. Thereafter blotting was further performed for one hour at 4° C., 70 V. 500 mA and 40 W. The gel was removed from the membrane and the membrane was washed twice in a washing buffer (0.05% Tween 20 in TBS, pH7.4). The membrane was blocked with a blocking buffer (3% skim milk, 0.05% sodium azide in TBS, pH7.4) for two hours at room temperature in order to prevent bonding to elements other than the antigen of primary antibodies. After blocking, it was washed twice in the washing buffer for 10 minutes at room temperature, and antibody-antigen reactions were performed for 2 hours at 4° C. using an anti-mouse albumin polyclonal antibody (Bio genesis, Cat# 0220-1829, Batch# 22062005) diluted 1000 times using an antibody incubation buffer (0.3% non-fat milk, 0.05% Tween 20 in TBS, pH7.4). Thereafter washing was performed in the washing buffer twice for 10 minutes at room temperature. A secondary antibody was prepared by diluting a peroxidase-labeled goat anti-rabbit IgG antibody (Jackson ImmunoResearch Laboratories, Code# 111-035-003) 3000 times with the antibody incubation buffer and reacting for 1 hour at room temperature. Thereafter washing was performed twice for twenty minutes using the wash buffer at room temperature. A perse signal was detected on the membrane using a Konica Immunostain HRP-1000 (Konica Corporation, Code# HRP-1000).

4. Quantification of Protein

The total cell protein concentration was measured using a BCA Protein Assay Reagent Kit (Pierce, Code# 23227). A BCA Protein Assay Reagent A (Pierce, Code# 23221) was well mixed with a BCA Protein Assay Reagent B (Pierce, Code# 23224) at a proportion of 50:1 and 200 µL of the mixed solution was applied to a microplate (Nalge Nunc International, Code# 269620). 50 µL of the sample was added to each well, stirred and incubated at 37° C. for 30 minutes. Absorbance was measured at 590 nm using a microplate reader (ImmunoMini NJ-2300, System Instrument Co. Ltd.). 2 mg/mL of bovine serum albumin (BSA; Nacalai tesque, Code# 012-02) was diluted as a standard solution to give the protein concentrations of 0, 31.25, 62.5, 125, 500, 1000 and 2000 µg/mL. An analytical curve was prepared and the protein concentration of the sample was calculated.

5. Method of PAS Staining (i) Test Reagent (1) 0.5% periodate aqueous solution; 0.5 g of periodate dihydrate (Nacalai tesque, Code# 26605-32) was dissolved in ultrapure water and the volume was made up to 100 mL.

(2) Schiff's reagent; 1 g of basic fuchsin (Wako Pure Chemicals, Code# 064-00582), 1g of sodium bisulfite (Nacalai tesque, Code# 312-20) and 1N hydrochloric acid were added to 20 mL of ultrapure water and dissolved while shielding against light and then the volume was made up to 200 mL with ultrapure water.

(3) sodium bisulfite (prepared as required); 6 mL of 10% sodium bisulfite and 5 mL of 1N hydrochloric acid were added to ultrapure water and the volume was made up to 100 mL using ultrapure water. The resulting solution was stirred for one hour or more.

The culturing solution was removed from the cultured cells and the cells were washed three times in 5 mL of PBS (−). After washing, 5 mL of 95% alcohol were added to the cells and the cells were allowed to stand for 30 minutes to fix. After 30 minutes, the concentration of alcohol was reduced to 80%, in 5 mL in one minute, then 70%, in 5 mL in one minute, then 50%, in 5 mL in one minute so as to gradually make the solution hydrophilic. Then finally the cells were washed in ultrapure water. After washing of the cells in completed, 0.5% of periodate aqueous solution was added to the cells and the cells were allowed to stand for 10 minutes. After 10 minutes, light washing was performed using ultrapure water, Schiffs reagent was added to the cells and the cells were allowed to stand for 10 minutes. After 10 minutes, without washing in water, 2% sodium bisulfite was added to the cells and the cells were allowed to stand for 1 minute. This operation was repeated three times and then washing was performed under running water. After washing in water, dehydration was performed by using 50% alcohol for three minutes, then 70% alcohol for two minutes, then 95% alcohol for two minutes, then 100% alcohol for 3 minutes. This operation was repeated three times. After dehydration, the cells were observed using an optical microscope.

6. Observation of Albumin Positive Cells Using Methods of Immunoflorescent Staining The medium was removed, 3 mL of PBS (−) was added and the cells were washed twice. After washing, 3 mL of PBS (−) containing 0.1% Triton X-100 was added to the cells and the cells were allowed to stand for 5 minutes. Ice-chilled 100% methanol was added and fixing of the cells was performed for one minute. The methanol was removed and blocking was performed by allowing the cells to stand for one hour in PBS (−) containing 5% skim milk. PBS (−) containing 5% skim milk was removed. 2 mL of rabbit anti-mouse albumin polyclonal antibody (Bio genesis, Cat# 0220-1829, Batch# 220620050) diluted 500 times using PBS (−) containing 5% skim milk was added to the cells and the cells were incubated for one hour. Washing was performed three times using PBS (−) containing 0.1% Triton X-100. 2 mL of secondary antibody (sheep anti-rabbit IgG FITC conjugated, MP Biomedicals Inc., Catalog# 55647, Lot# 02756) diluted 500 times using PBS (−) containing 5% skim milk was added to the cells and the cells were incubated for one hour while shielding against light. Washing was performed three times in the washing buffer and the signal was observed using an inverted research microscope (OLYMPUS, IX71).

7. Deactivating uPA using Diisopropyl Fluorophosphate (DFP)

DFP (Wako Pure Chemicals, Code# 046-28561, Lot# CEE3951) is a substance which is rapidly degraded in aqueous solutions, so that the dissolution and dilution of DFP was performed using isopropanol. DFP was added to 3000 U/mL of uPA (Mochida Pharmaceutical Co., Ltd) to make a final concentration of 5 mM. After adding DFP, the solution was allowed to stand at room temperature for two hours. Then the entire solution was transferred into a cellulose dialysis tube, (Wako Pure Chemicals, Code# UC36-32-100) and dialysis was performed against 1 L of PBS (−) for 24 hours at 4° C. During this period, the outer liquid was exchanged twice. After completing dialysis, deactivation of uPA was confirmed using zymography and fibrin plate. Then after checking, the uPA was filter-sterilized and used for culture supplemented experiments.

8. Analysis of Albumin Positive Cells Using Fluorescence Activated Cell Sorting (FACS)

The medium of the cultured cells was removed and washing was performed using PBS (−). After the cells were detached from the surface of the dish using 0.25% trypsin solution, 5 mL of a collagenase solution as described below was added to the cells and the cells were incubated at 37° C. for 30 minutes in order to digest the intercellular adhesion.

Collagenase Solution

Trypsin Inhibitor 5 mg (Sigma, Trypsin Inhibitor, Type 11-0: Chicken Egg White, Code# 232-906-9)
collagenase 50 mg (Wako, catalog# 035-17604, Lot# CEH0328) HEPES 0.238 g,
100 mL Hank's Solution containing $NaHCO_3$ 0.035 g (Nissui Pharmaceutical Co., Ltd., Code# 05906)

Figure 12:
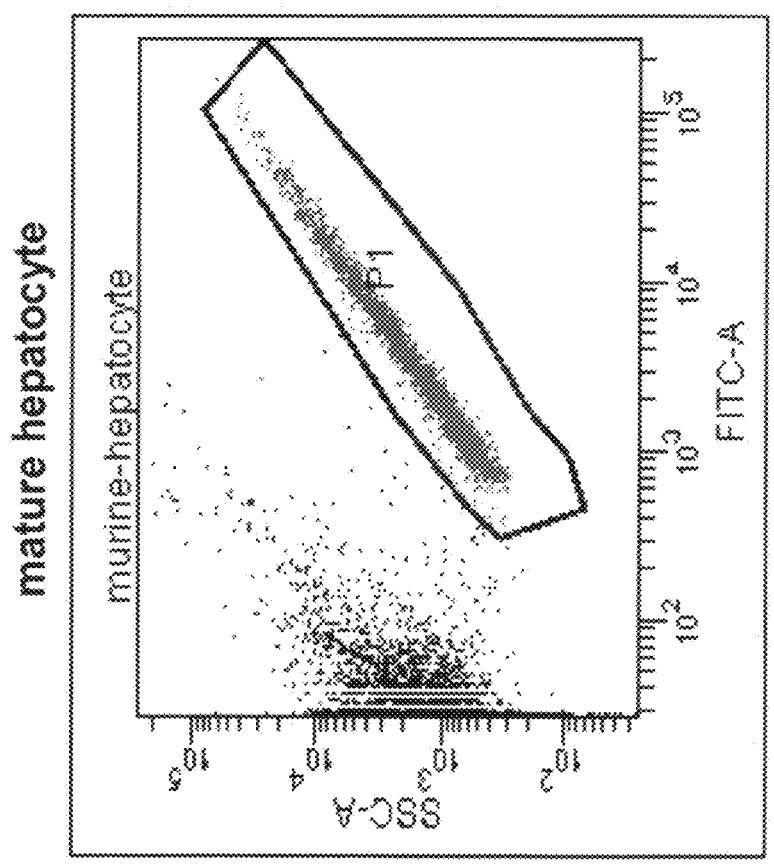
FIG. 12 shows the result of FACS analysis of murine mature hepatocytes.

After digestion, cells were collected by centrifugation (1000 rpm, 4° C., 5 minutes) and fixed using 1 mL of ice-chilled 100% methanol. After fixing the cells, centrifugation (1500 rpm, 4° C., 5 minutes) was performed in order to remove the methanol. 500 µL of PBS (−) was added to the cells, then 1 µL of rabbit anti-mouse albumin polyclonal antibody (Bio genesis, Cat# 0220-1829, Batch# 22062005) was added and the cells were allowed to stand at room temperature for one hour. Then FITC-bonded sheep anti-rabbit IgG (MP Biomedicals Inc., Catalog# 55647, Lot# 02756) was added to the cells and the cells were allowed to stand for one hour while shielding against light. After standing for one hour, the cells were loaded by a FACS Canto™ (Becton Dickinson, Franklin Lakes, N.J.) wherein a FSC voltage was set to 80, a FITC voltage was set to 300 and a threshold was set to 1000. Thereafter BD DiVa Software was used for analysis. In FIGS. 12 and 13, the intensity of FITC is shown on the horizontal axis and FSC is shown on the vertical axis.

9. Method of Cell Transplantation of Differentiated Cells originating from ES Cells by Methods of Liver Cell Transplantation via the Spleen, and a Method of Examination As described above, TT2 cells used in the Examinations are the established ES cells originating from male mice by crossing C57/BL6 mouse with CBA mouse. A C57/BL6 female mouse was used as the recipient in cell transplantation experiments. An EB was prepared using a hanging drop method, inoculated onto a collagen-coated dish and cultured in order to induce differentiation. The resulting EB was ES cells for transplantation. Culturing to induce differentiation was performed for 18 days under conditions with uPA supplement or without uPA supplement (control). Trypsin and collagenase treatment was performed to separate the cells.

The procedure of methods for liver transplantation via the spleen is shown in FIG. 14. 100 µL of 20% carbon tetrachloride ($CCl_4$) solution (supplemented with 80 µL olive oil for each 20 µL of $CCl_4$) was administered intraperitoneally per 20 g of mouse body weight (20 µL $CCl_4$/20 g mouse body weight) in order to induce liver damage. Six hours after the carbon tetrachloride injection, 100 µL of a suspended solution of differentiated cells originating from ES cells ($5\times10^6$ cells/mL) was infused via the spleen. 14 days after the transplantation, the liver and spleen were excised and morphology was examined for the presence or absence of teratoma. Total RNA was also purified from two positions including the teratoma forming section when teratoma was present in the organ. When teratoma was not observed, total RNA was purified from the central section and edge of the lobe of the liver, and from the lower extremity and central extremity obtained by dividing the spleen equally into three parts. RT-PCR was used to confirm the expression of the sex-determining region on Y chromosome (SRY) in order to confirm whether the cells of male mouse origin have been implanted into the organ (Kidokoro T et al., Dev Biol. 2005 Feb. 15; 278(2):511-25.). Furthermore the expression of Oct-4 was confirmed in order to check whether the implanted cells were undifferentiated or differentiated.

Example 1

Formation of an Embryoid Body by Hanging Prop Method and Induction of Differentiation to Hepatocyte In this example, experiments were performed using TT2 ES cells of mouse origin as model cells. The formation of an embryoid body (EB) from an ES cell was performed using a hanging drop method. After starting hanging drop culturing, the five day EB was inoculated onto a collagen-coated dish and cultured using IMDM containing 20% FBS in order to induce differentiation into hepatocyte.

FIG. 2 shows the results of the expression analysis of the various differentiation markers in an ES cell induced to differentiate by the hanging drop method. After isolating the total RNA from the cells induced differentiation, the expression of various types of the differentiation markers was observed using RT-PCR.

In FIG. 2, Oct-4 denotes octmer binding protein-4, CK-19 denotes cytokeratin 19, AFP denotes α-fetoprotein, TTR denotes transthyretin, A1b denotes albumin, AAT denotes α1-antitrypsin, CMA denotes cardiac muscle actin and GAPDH denotes glyceraldehyde 3-phosphate dehydrogenase.

When the ES cells were cultured in the above manner, the expression of the marker for undifferentiated cells Oct-4 was no longer found in EBs after six days when differentiation was induced in a collagen-coated dish. The expression of the differentiation markers for hepatocytes such as albumin or α-fetoprotein and the differentiation marker genes for differentiation of the cardiac muscle mesoderm such as cardiac muscle actin (CMA) were induced by culturing of EB formed by the hanging drop method in a collagen-coated dish. It was found that CMA, a cardiac muscle marker, was expressed at an earlier stage than the differentiation marker for hepatocytes. Furthermore it was shown that the ES cell at 18 days after commencement of EB formation displayed a higher level of differentiation of ES cells into hepatocytes.

After the $18^{th}$ day of culturing in differentiation-inducing medium, the cells incorporated indocyanine green and were stained with it. The results are shown in FIG. 3. The photograph on the right of FIG. 3 is an enlargement of section inscribed with a square in the left photograph. The arrowheads in the left photograph show cardiac muscle-like cells and the arrow in the right photograph shows hepatocyte-like cells.

Figure 4:
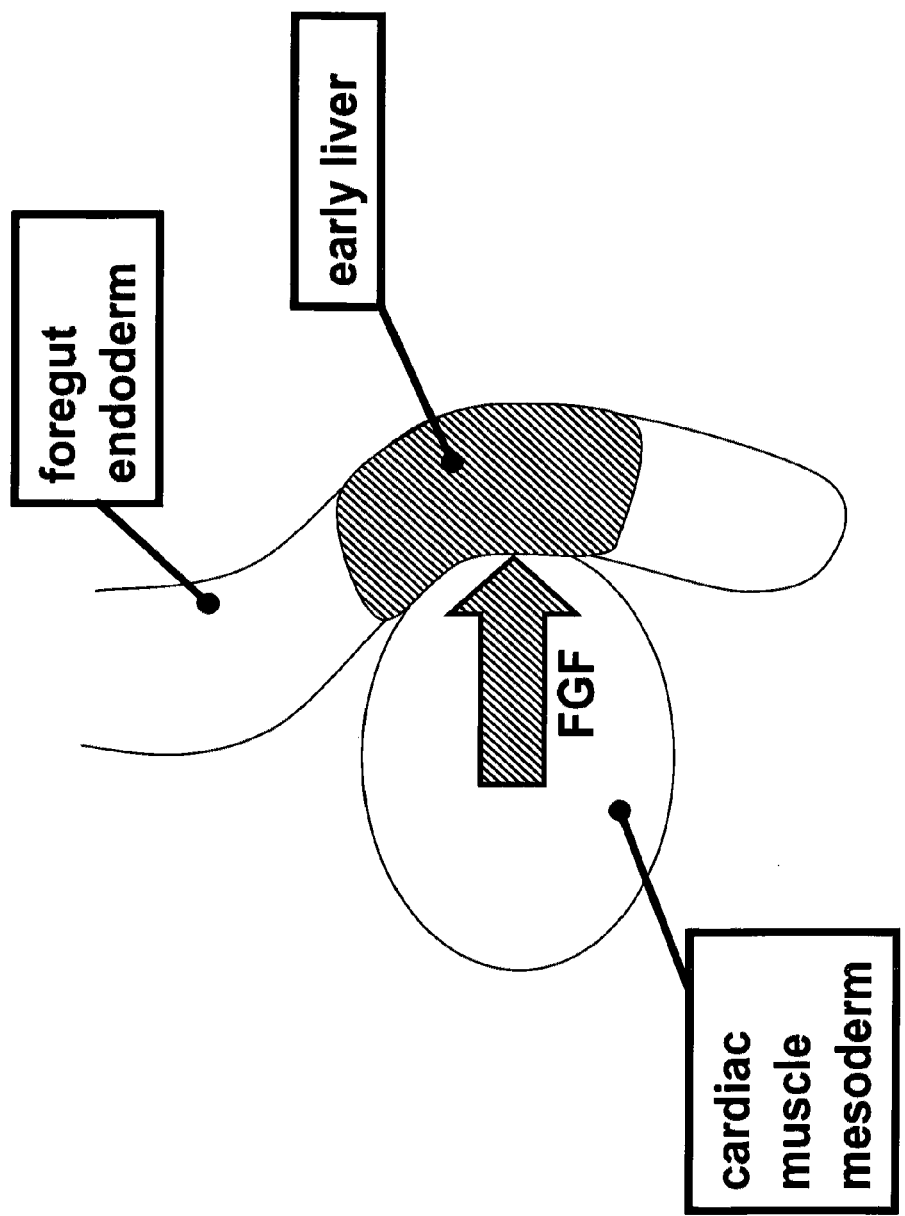
FIG. 4 is a schematic representation showing the role of cardiac muscle mesoderm in the development of hepatocytes.

Thus the cells having the large nucleus which is characteristic for hepatocytes were observed. Furthermore many cells incorporating indocyanine green in the periphery of the pulsating cardiac muscle-like cells, that is to say, hepatocytes were observed. This phenomenon is very similar to the phenomenon during development in which the foregut endoderm which is in contact with cardiac muscle mesoderm differentiates into hepatocytes (FIG. 4). It has been recently reported that during development, FGF which is secreted by cardiac muscle plays an important role in the development of the hepatocytes.

This example demonstrates the possibility of inducing hepatocytes from ES cells by forming an EB and culturing ES cells. This type of culturing shows that differentiation into hepatocytes is promoted firstly by the formation of cardiac muscle cells and then by some type of promoting factor originating in the cardiac muscle.

In Examples 2-6 hereafter, the effect of FGF which is clearly important for liver development and uPA on the differentiation of ES cells into hepatocytes was examined.

EB prepared by the hanging drop method was inoculated on a collagen-coated dish. When inoculating, aFGF (Sigma, code # F5542, final concentration 20 ng/mL) and human uPA (Mochida Pharmaceutical Co., Ltd, final concentration 10 u/mL) were added and culturing was performed in order to examine any effect on differentiation into a hepatocyte. The examination of the level of differentiation into hepatocytes was performed with reference to not only the expression of the proteins or the marker genes which are specific to hepatocytes (Examples 2, 3 and 5) but also with reference to glycogen storage cells stained using PAS (Example 4), and albumin-producing cells using immunoflorescent staining (Example 4). In addition, FACS analysis was used to examine qualitative and quantitative changes in albumin producing cells and to contrast with mature murine hepatocytes isolated by collagenase perfusion methods (Example 6).

Example 2

Changes in the Level of Expression of various Genes and Proteins Resulting from Addition of FGF Receptor Inhibitor or aFGF This example focused on FGF which participates in early-stage liver development and examined the effect of FGF on inducing differentiation of ES cells.

The cells were cultured for 18 days using differentiation-inducing medium supplemented with aFGF or Su402 which is a FGF receptor inhibitor. After culturing, RT-PCR was used to observe the expression of the various differentiation markers. The level of protein expression was analyzed using western blot analysis.

Figure 5:
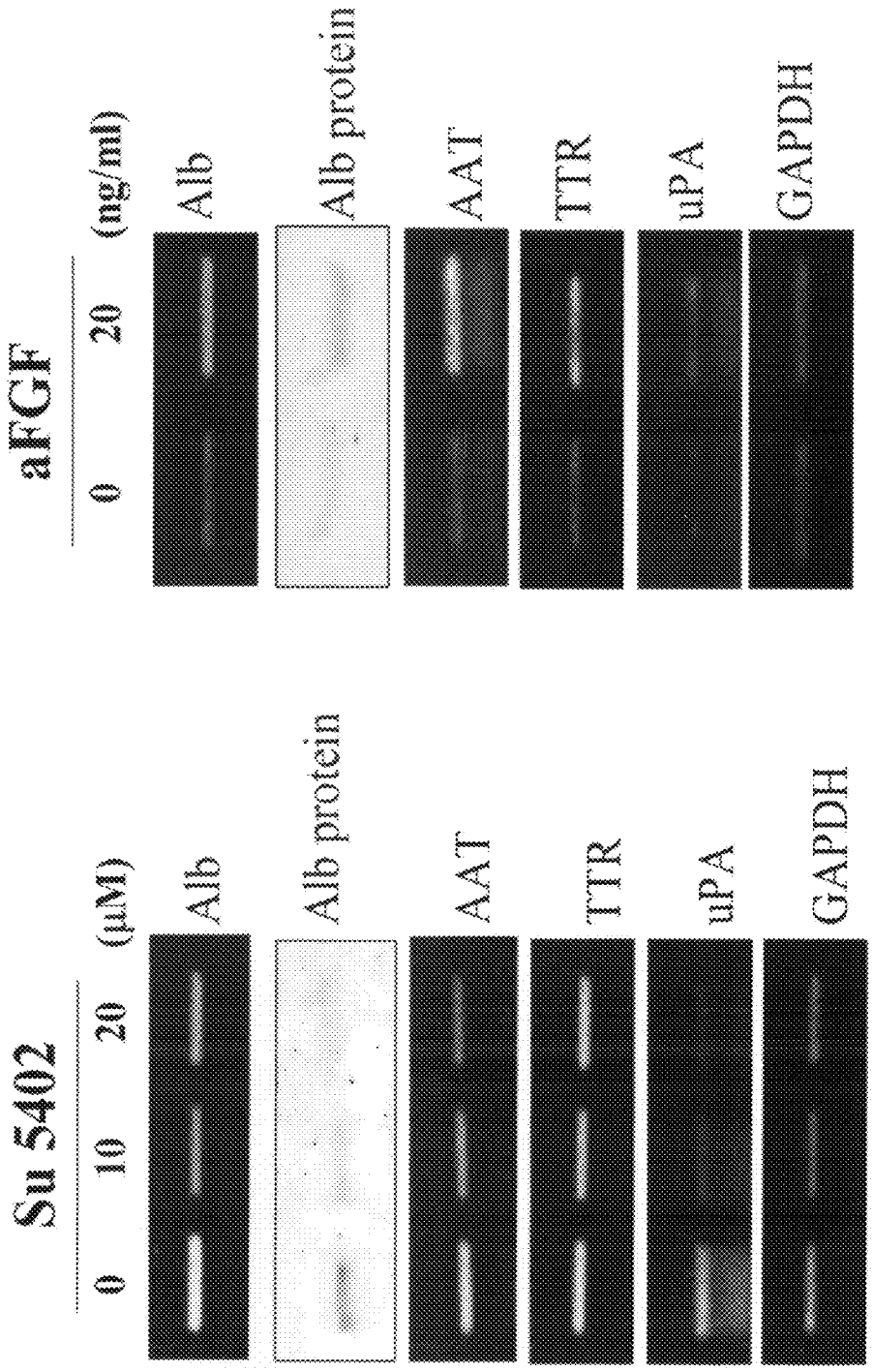
FIG. 5 shows changes in the level of expression of the differentiation markers resulting from supplementation of aFGF, and Su5402, an FGF receptor inhibitor.

In FIG. 5, A1b denotes albumin, AAT denotes α1-antitrypsin, TTR denotes transthyretin, uPA denotes urokinase-type plasminogen activator, and GAPDH denotes glyceraldehyde 3-phosphate dehydrogenase.

Culturing of EB produced by the hanging drop method in a collagen-coated dish in the presence of aFGF resulted in a significant increase in the expression of the various differentiation markers for hepatocyte such as albumin or cytochrome P450 7A1 (Cyp7a1) (data not shown) (FIG. 5).

The addition of Su5402, which is the inhibitor of aFGF receptor signaling, suppressed the differentiation markers for hepatocyte in a concentration-dependent manner.

These results show that when aFGF induces differentiation of ES cells into hepatocytes, differentiation of ES cells into hepatocytes is promoted through signals from the FGF receptor.

Example 3

Changes in the Level of Expression of Various Genes or Proteins Resulting from Addition of uPA or uPA-Activity Inhibitor (p-aminobenzamidine)

In view of the fact that FGF has been reported to induce the expression of uPA gene, this example examined the effect of the addition of uPA on the differentiation of ES cells.

The cells were cultured for 18 days using differentiation-inducing medium supplemented with uPA or p-aminobenzamidine which is an uPA activity inhibitor. After culturing, RT-PCR was used to observe the gene expression of the various differentiation markers. The level of protein expression was analyzed using western blot analysis.

Figure 6:
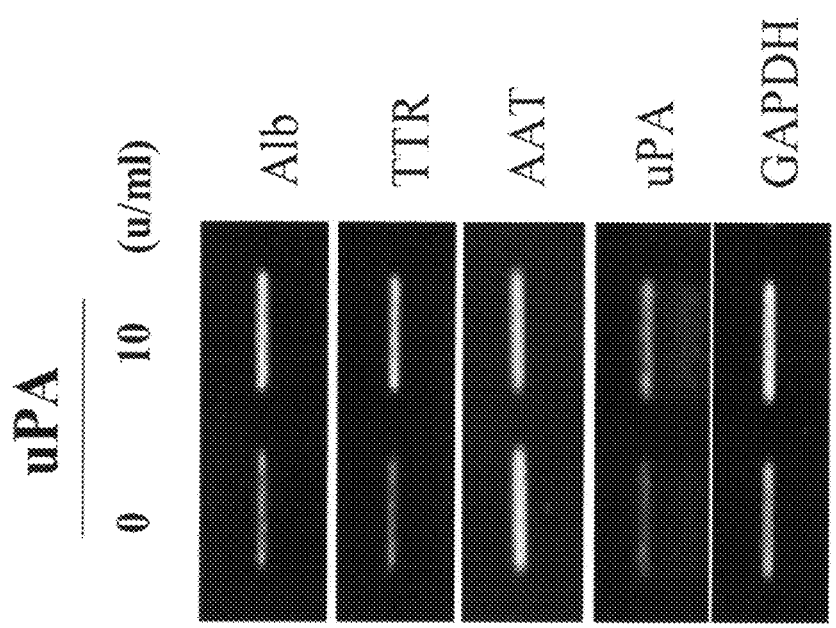
FIG. 6 shows changes in the level of expression of the differentiation markers resulting from supplementation of uPA.

In FIGS. 6 and 7, A1b denotes albumin, TTR denotes transthyretin, AAT denotes α1-antitrypsin, AFP denotes α-fetoprotein, uPA denotes urokinase-type plasminogen activator, GAPDH denotes glyceraldehyde 3-phosphate dehydrogenase, Cyp7a1 denotes cytochrome P450 7A1 and CMA denotes cardiac muscle actin.

Similarly to the results for aFGF, the results show that uPA increases the expression of albumin and Cyp7a1 (data not shown) and induces differentiation into hepatocyte (FIG. 6).

The expression of the hepatocyte markers was suppressed by the addition of p-aminobenzamidine (p-ab) which is an uPA activity inhibitor (final concentration, 100 μM or 200 μM) (FIG. 7).

On the other hand, uPA pretreated with diisopropyl fluorophosphate (DFP) which inhibited uPA activity or tissue-type PA which has the same substrate specificity as uPA, did not induce differentiation into hepatocytes. These results show that there is a high probability that uPA activity is required for differentiation into hepatocytes.

Next, time-dependent variations in trends of the gene expression resulting from addition of uPA were examined.

The cells were cultured for 18 days using differentiation-inducing medium with or without uPA supplement. RT-PCR was used to observe the expression of the various differentiation markers.

In FIG. 8, A1b denotes albumin, Cyp7a1 denotes cytochrome P450 7A1, CMA denotes cardiac muscle actin and GAPDH denotes glyceraldehyde 3-phosphate dehydrogenase.

As a result, the expression of the hepatocyte differentiation marker (Cyp7a1) in control cells not supplemented with FGF or uPA was increased after the peak in the expression of CMA which is a differentiation marker for cardiac muscle. This result shows that a type of promoting factor produced by cardiac muscle cells is required for differentiation into hepatocytes (FIG. 8).

On the other hand, addition of uPA resulted in an increase in the expression of the hepatocyte differentiation marker before the CMA expression reached a peak (FIG. 8).

This example demonstrates for the first time that differentiation of ES cells into hepatocytes is induced by uPA.

Example 4

Observation of Glycogen Storing Cells Using Pas Staining and Observation of Albumin Producing Cells using Immunoflorescent Staining In this example PAS staining of glycogen storing cells and immunoflorescent staining of albumin was performed on control cells to which uPA or FGF had not been added and on cells to which uPA had been added.

Figure 9:
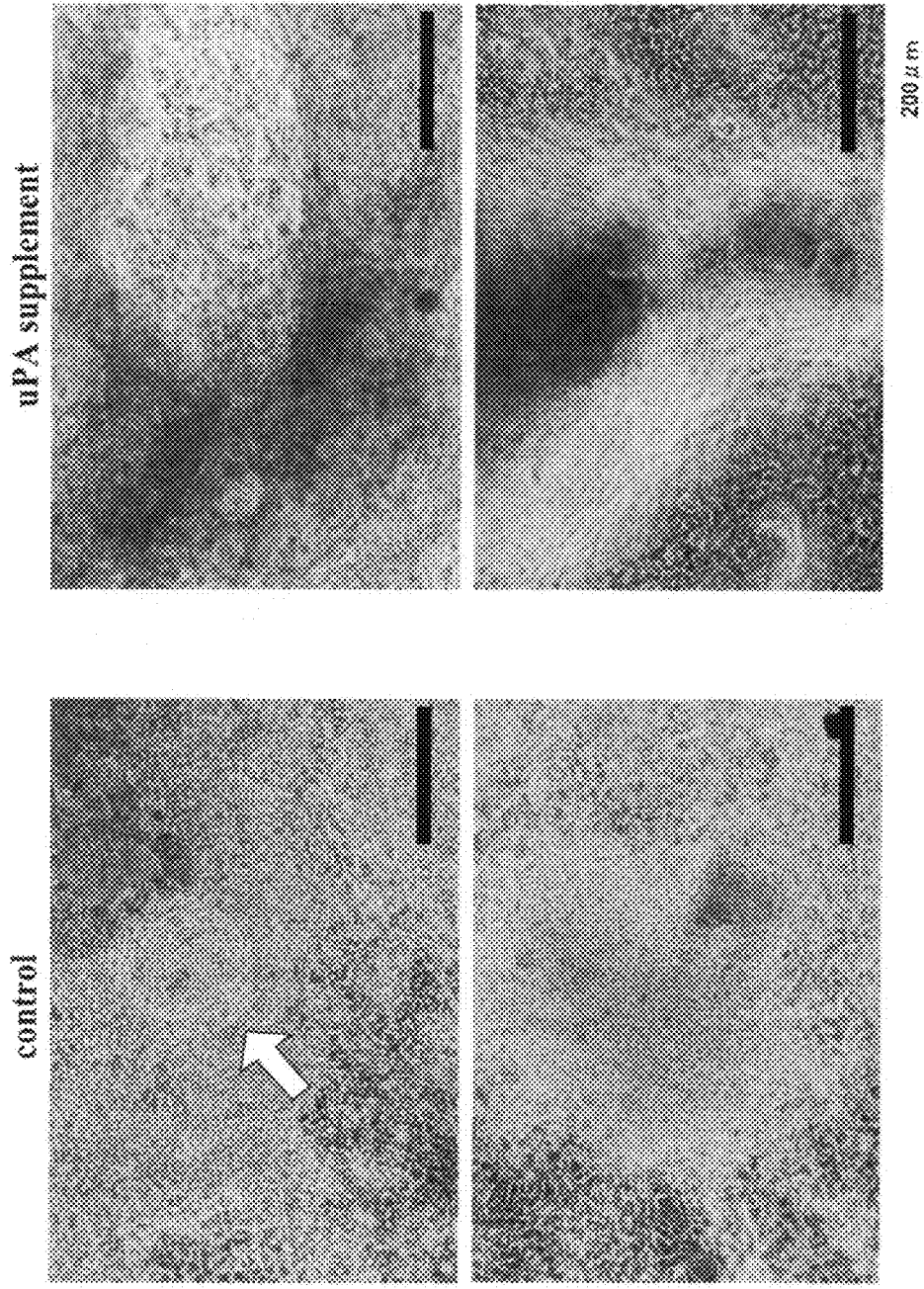
FIG. 9 shows PAS staining of glycogen storing cells.
Figure 10:
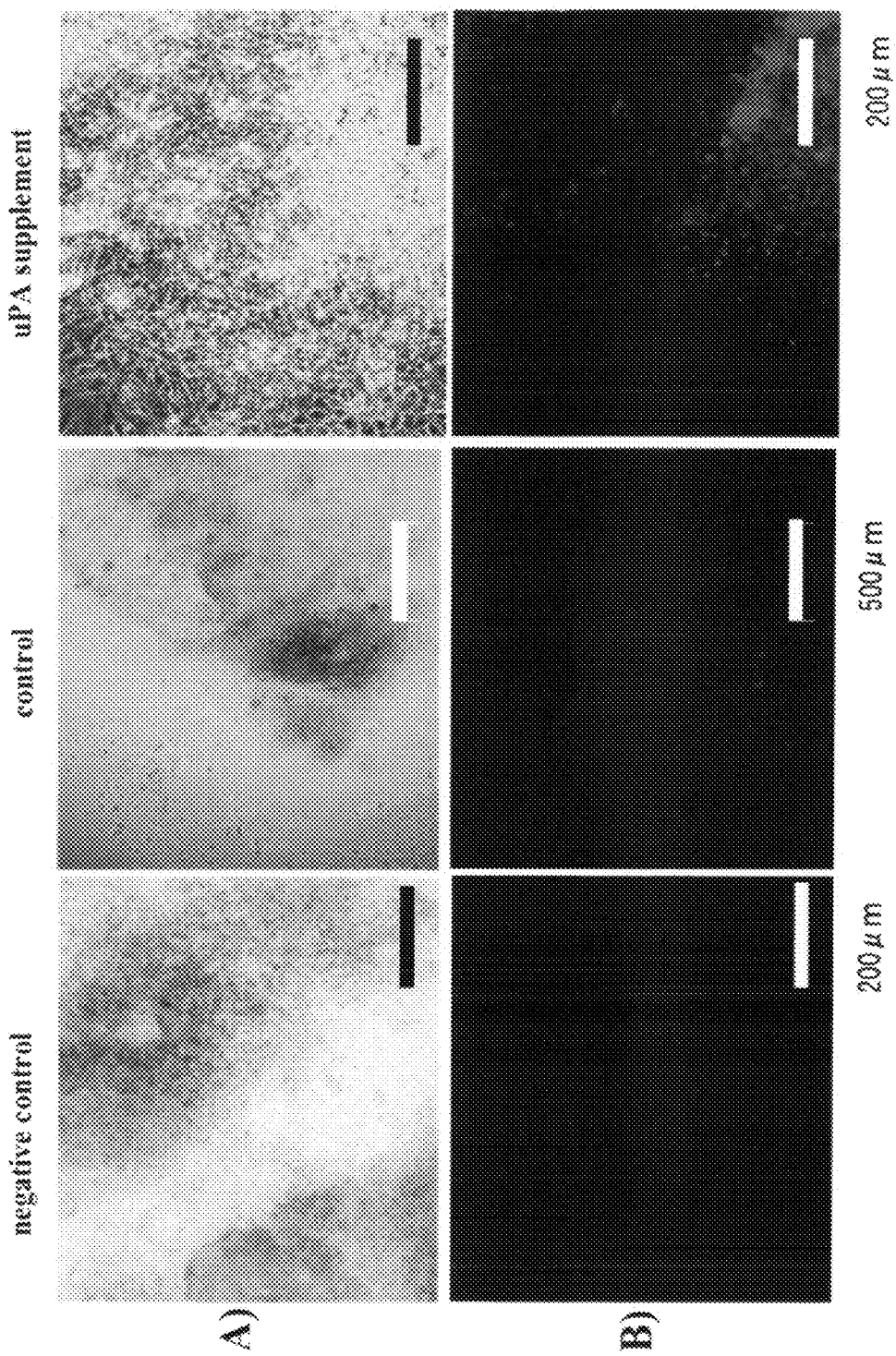
FIG. 10 shows immunoflorescent staining of albumin.

The cells were cultured using differentiation-inducing medium without uPA supplement or with 10 u/mL uPA supplement. PAS staining was performed on the $15^{th}$ day. In the $9^{th}$ day of culturing, anti-albumin antibodies were used to detect albumin producing cells (green). The results of PAS staining are shown in FIG. 9. The white arrow shows cardiac muscle-like cells. The immunoflorescent staining image of albumin is shown in FIG. 10. FIG. 10(A) shows the bright field image, (B) shows the fluorescent image. The left image in FIG. 10 shows the result of ES cells not being induced to differentiate.

These results show that in the control cells, glycogen granule positive cells which are positive for PAS staining are localized in the periphery of cardiac muscle cells. In contrast, in the cells supplemented with uPA, many glycogen granule positive cells are also observed outside the periphery of cardiac muscle cells (FIG. 9). When compared with the control cells, a stronger PAS staining image was detected in the cells supplemented with uPA.

Almost no expression of albumin was detected in the control cells. Cells expressing albumin were well localized with PAS stain positive cells and observed at multilayer sections of the cells. Observation also demonstrated an increase of albumin-positive cells resulting from addition of uPA (FIG. 10).

Example 5

Changes in the Level of Gene Expression Resulting from Addition of uPA, DFP-Treated uPA or tPA The cells were cultured for 18 days using differentiation-inducing medium supplemented with such factors as uPA, DFP-treated uPA (DFP-uPA) or tPA or without any supplement (cont). uPA is deactivated by treatment with DFP. RT-PCR was used to observe the expression of the various differentiation markers.

Figure 11:
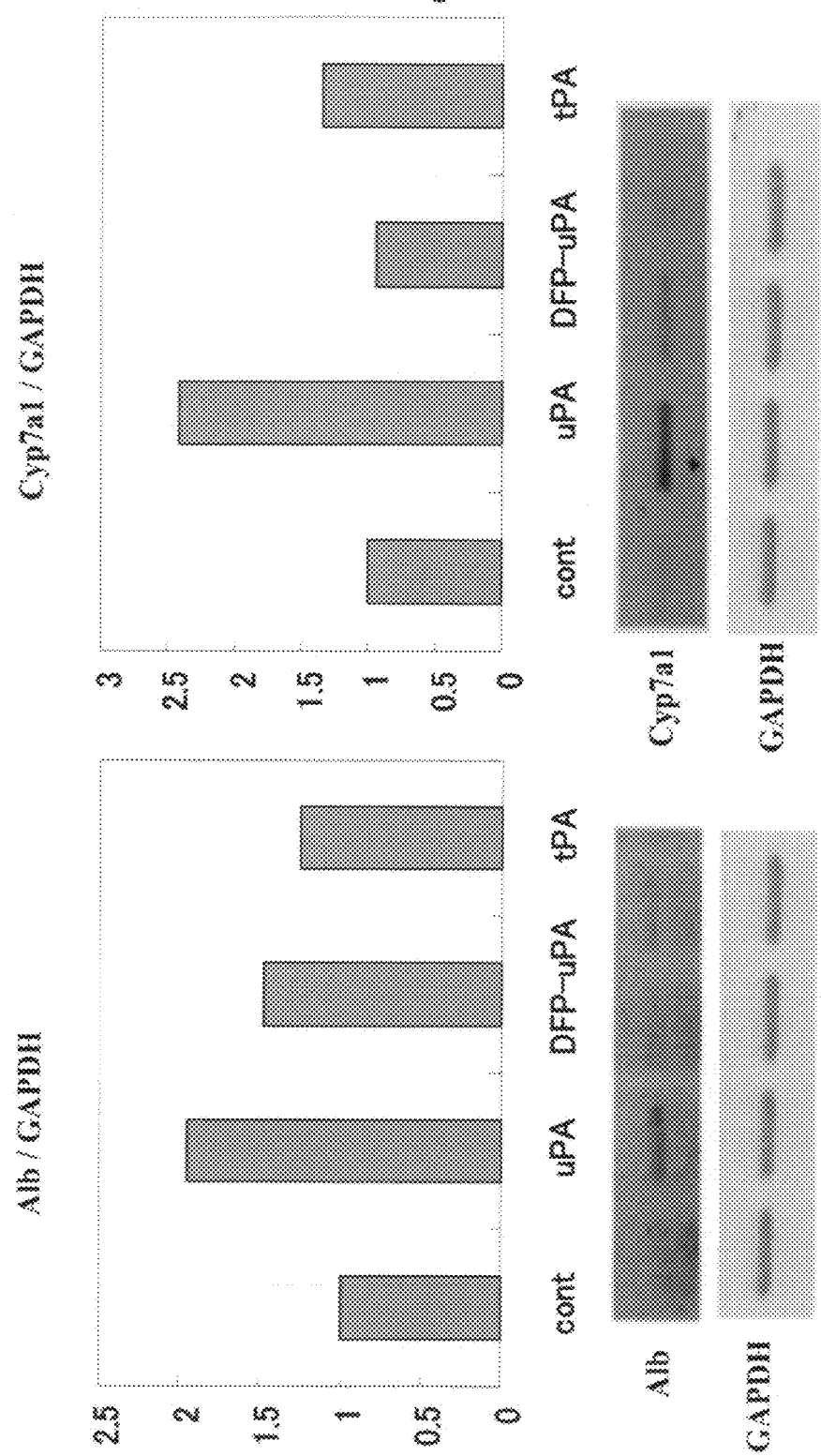
FIG. 11 shows changes in the level of gene expression resulting from supplementation of uPA, DFP-treated uPA and tPA.

The results show that the addition of uPA increases the level of expression of albumin or Cyp7a1 which are the hepatocyte differentiation markers (FIG. 11). Addition of DFP-uPA or tPA resulted in almost no change in the expression of the hepatocyte differentiation markers (FIG. 11).

Example 6

Analysis of Albumin Producing Cells

In this example, cell producing albumin which is an expression marker for hepatocytes was analyzed using FACS. In other words, FACS was used to examine whether cells differentiated due to uPA addition have the same characteristics as hepatocytes.

Firstly FACS analysis was used on mature murine hepatocytes. The FACS analysis was performed using anti-albumin antibodies with respect to mature murine hepatocytes prepared using a collagenase reflux method. The results show that groups of albumin positive cells are identified in the mature murine hepatocytes (FIG. 12).

Then uPA, DFP-treated uPA or tPA was added to differentiation-inducing medium and cultured for 9 days. Cells were isolated using trypsin treatment and collagenase treatment, and FACS analysis was performed using anti-albumin antibodies.

The results show that there is an increase in the number of cells producing albumin among the differentiated cells of ES cell origin with added uPA in comparison to the control (FIG. 13). The group of cells producing albumin is of almost the same size and produce almost the same amount of albumin as mature hepatocytes separated from mice. Albumin producing cells accounted for 22% of the total number of cells differentiated from ES cells (Cont). The number of albumin producing cells was increased to 52% of the total number of cells when differentiation of the cells was induced by supplement of uPA.

Furthermore albumin producing cells account for 27.8% of the total number of cells supplemented with DFP-treated uPA (DFP-uPA) and 27.2% of cells supplemented with tPA.

Thus the results demonstrate that only uPA promotes the induction of an ES cell into a hepatocyte.

Example 7

Morphological Observation of the Spleen and Liver after Transplantation and RT-PCR Analysis of Differentiation Markers Cell transplantation into mice was performed on (i) a group wherein ES cells maintained in an undifferentiated state by not culturing to induce differentiation were used, (ii) a group wherein control cells not induced to differentiate by addition of uPA were used, and (iii) a uPA group wherein cells induced to differentiate by addition of uPA were used to transplant. The ES cell transplantation group was transplanted into four mice and the other groups were transplanted into three mice. Organs were recovered 14 days after transplantation and examined for formation of teratomas.

After cell transplantation, total RNA was recovered from the liver and spleen and RT-PCT was effected to measure the various gene expressions. In organs displaying teratoma formation, total RNA was isolated from the position of teratoma formation. In livers not displaying teratoma formation, total RNA was isolated from the central section and edge of the lobe of the liver. In the spleen, total RNA was isolated from the lower extremity and central extremity obtained by dividing the spleen equally into three parts.

The results are shown in Table 1. In Table 1, Oct-4 denotes octmer binding protein-4 and SRY denotes sex-determining region Y gene.

TABLE 1

|  | uPA(−) | uPA(+) |
|---|---|---|
| Formation of Teratoma in Liver | 3/3 | 0/3 |
| SRY Gene | 3/3 | 2/3 |
| Oct-4 Gene | 3/3 | 0/3 |
| Formation of Teratoma in Spleen | 1/3 | 0/3 |
| SRY Gene | 1/3 | 1/3 |
| Oct-4 Gene | 0/3 | 0/3 |

For the mice group of transplanted control cells (uPA(−)), teratomas formed in three out of three mice. In the spleen into which cells were infused, formation of teratoma was confirmed in one out of three mice. On the other hand, in the group of cells supplemented with uPA (uPA(+)), no mouse had a confirmed teratoma formation in the liver. Likewise there was not teratoma formation in the spleen. Teratomas were observed in all cases in which ES cells maintained in an undifferentiated state by not culturing to induce differentiation were used for cell transplantation.

The expression of SRY gene which is a male marker was confirmed in the liver of three out of three mice having Control cell (uPA(−)) transplantations. This shows that the male-originated cells used in cell transplantation were implanted into the liver of the female mice. The expression of Oct-4, the marker for undifferentiated cells was also confirmed in three out of three mice. SRY expression in the spleen was only confirmed in one out of three mice. There was no confirmation of Oct-4 expression in the spleen. Although Oct-4 expression was not observed, there is a strong possibility that the cells used in the transplantation caused of teratoma formation.

On the other hand, SRY gene expression in livers of the group with uPA supplement (uPA(+)) was confirmed in two out of three mice and Oct-4 gene expression in zero out of three mice. SRY gene expression in spleens was confirmed in one out of three mice and Oct-4 expression in zero out of three mice. These results demonstrate that when differentiation is induced by addition of uPA, there is a decrease in the incidence of teratoma formation associated with cell transplantation.

In this example, the rate of teratoma formation was decreased when the cells were differentiated using uPA and transplanted into a mouse via spleen. Furthermore Oct-4 gene expression which is the undifferentiation marker was not observed. When cell induced to differentiate not in the presence of uPA are transplanted, teratomas formed in the liver or spleen. Since Oct-4 expression was observed in these organs, the differentiation level of these transplanted cells was low in comparison with those of cells differentiated using uPA. Therefore it is hypothesized that cells not differentiated using uPA contain a larger number of more undifferentiated cells, differentiate into various cell types within the implanted organ and result in formation of teratomas. Therefore cells differentiated using uPA have a higher level of differentiation in comparison with cells differentiated using conventional methods.

This example demonstrates that transplants are possible by using ES cells which are differentiated into specific functional cells, preferably with a high level of differentiation.

Industrial Applicability

This invention provides an agent comprising uPA for promoting effective differentiation of an ES cell, or preferably an agent for promoting differentiation of an ES cell into a hepatocyte, or a method of promoting effective differentiation of an ES cell, or preferably a method of promoting differentiation of an ES cell into a hepatocyte. Furthermore this invention provides a method of preparing a hepatocyte. In another aspect, this invention provides a method of transplanting with a low probability of developing teratoma. Furthermore this invention provides a prophylactic agent for teratoma and a method of preventing teratoma.

This invention discloses for the first time that differentiation from an ES cell into a hepatocyte is induced by uPA and that it is possible to differentiate effectively from an ES cell into a hepatocyte using uPA.

This invention may preferably provide a solution for various problems related to transplantation therapies such as lack of donors, rejection or organ donor tissue loss.

Furthermore the hepatocytes obtained using this invention are preferably more highly differentiated than cells obtained using conventional methods of inducing differentiation. Consequently this invention preferably provides hepatocytes which are more adapted for transplantation therapies with low risk of developing teratoma (teratoid tumors) caused by transplantation.

The invention claimed is:

1. A method of promoting differentiation of ES cells into hepatocytes comprising:
   (a) culturing ES cells under a suitable condition to form an embryoid body (EB); and
   (b) culturing the EB on a collagen-coated dish in a differentiation-inducing medium comprising; active urokinase-type plasminogen activator to induce the formation of hepatocytes.

2. A method of preparing hepatocytes comprising:
   (a) culturing ES cells under a suitable condition to form an embryoid body (EB);
   (b) culturing the EB on a collagen-coated dish in a differentiation-inducing medium comprising active urokinase-type plasminogen activator to induce the formation of hepatocytes; and
   (c) collecting said hepatocytes.

* * * * *